United States Patent
Muratori et al.

(10) Patent No.: US 10,792,088 B2
(45) Date of Patent: Oct. 6, 2020

(54) METHODS AND DEVICES FOR USING SUB-MICROSECOND ELECTRIC PULSES TO TRIGGER APOPTOSIS

(71) Applicant: Old Dominion University Research Foundation, Norfolk, VA (US)

(72) Inventors: Claudia Muratori, Virginia Beach, VA (US); Andrei G. Pakhomov, Norfolk, VA (US); Olga N. Pakhomova, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 244 days.

(21) Appl. No.: 15/789,727

(22) Filed: Oct. 20, 2017

(65) Prior Publication Data
US 2018/0110557 A1   Apr. 26, 2018

Related U.S. Application Data

(60) Provisional application No. 62/417,498, filed on Nov. 4, 2016, provisional application No. 62/410,782, filed on Oct. 20, 2016.

(51) Int. Cl.
*A61B 18/14* (2006.01)
*A61B 18/00* (2006.01)
(Continued)

(52) U.S. Cl.
CPC .......... *A61B 18/1206* (2013.01); *A61B 18/02* (2013.01); *A61B 18/1477* (2013.01);
(Continued)

(58) Field of Classification Search
CPC . A61B 18/1206; A61B 18/02; A61B 18/1477; A61B 2018/00011;
(Continued)

(56) References Cited

U.S. PATENT DOCUMENTS

| 6,326,177 B1 | 12/2001 | Schoenbach et al. |
| 6,831,377 B2 | 12/2004 | Yampolsky et al. |

(Continued)

FOREIGN PATENT DOCUMENTS

WO   2018/075946 A1   4/2018

OTHER PUBLICATIONS

Marie-Pierre Rols, Temperature effects on electrotransfection of mammalian cells Dec. 13, 1993, Nucleic Acids Research, vol. 22 No. 3, p. 540.*

(Continued)

*Primary Examiner* — Linda C Dvorak
*Assistant Examiner* — Annabeth E Rodriguez
(74) *Attorney, Agent, or Firm* — Kilpatrick Townsend & Stockton LLP

(57) ABSTRACT

The methods disclosed herein are directed towards improving ablation efficiency associated with applying nanosecond electric pulses (nsEP) to tissue. In particular, applying nsEP to tissue can open pores in the cellular membranes of the tissue. These pores can be kept open longer by cooling the tissue. The combined application of nsEP and the cooling of tissue may have synergistic effects on triggering apoptosis of cells in the tissue. This allows for numerous practical benefits associated with nsEP-based tissue ablation to be realized. For instance, nsEP of lower pulse strength or lower numbers of pulses to be used, which can be provided by smaller pulse generators operating on less power.

25 Claims, 22 Drawing Sheets

(51) Int. Cl.
　　　*A61B 18/02*　　　(2006.01)
　　　*A61B 18/12*　　　(2006.01)

(52) U.S. Cl.
　　　CPC .............. *A61B 2018/00011* (2013.01); *A61B 2018/00577* (2013.01); *A61B 2018/00702* (2013.01); *A61B 2018/00726* (2013.01); *A61B 2018/00761* (2013.01); *A61B 2018/143* (2013.01); *A61B 2018/1425* (2013.01)

(58) Field of Classification Search
　　　CPC ........... A61B 2018/00577; A61B 2018/00702; A61B 2018/00761; A61B 2018/00726; A61B 2018/1425; A61B 2018/143
　　　See application file for complete search history.

(56) References Cited

U.S. PATENT DOCUMENTS

| | | | |
|---|---|---|---|
| 7,767,433 | B2 | 8/2010 | Kuthi et al. |
| 8,000,813 | B2 | 8/2011 | Schoenbach et al. |
| 8,512,334 | B2 | 8/2013 | Nuccitelli et al. |
| 8,822,222 | B2 | 9/2014 | Beebe et al. |
| 9,101,764 | B2 | 8/2015 | Nuccitelli et al. |
| 9,168,373 | B2 | 10/2015 | Nuccitelli et al. |
| 9,724,155 | B2 | 8/2017 | Nuccitelli et al. |
| 9,918,790 | B2 | 3/2018 | Zemlin et al. |
| 10,070,914 | B2 | 9/2018 | Schoenbach et al. |
| 10,097,085 | B2 | 10/2018 | Cadilhon et al. |
| 10,252,050 | B2 | 4/2019 | Kreis et al. |
| 2006/0062074 | A1 | 3/2006 | Gundersen et al. |
| 2006/0212032 | A1* | 9/2006 | Daniel ................ A61B 18/148 606/41 |
| 2007/0129714 | A1* | 6/2007 | Elkins .................... A61B 18/02 606/21 |
| 2008/0031337 | A1 | 2/2008 | Hasegawa et al. |
| 2010/0038971 | A1 | 2/2010 | Sanders et al. |
| 2010/0049178 | A1* | 2/2010 | Deem .................... A61B 18/02 606/9 |
| 2010/0331758 | A1 | 12/2010 | Davalos et al. |
| 2011/0160514 | A1 | 6/2011 | Long et al. |
| 2013/0260435 | A1* | 10/2013 | Pakhomova ........... C12N 13/00 435/173.6 |
| 2014/0277219 | A1* | 9/2014 | Nanda ..................... A61N 1/403 607/3 |
| 2015/0065946 | A1 | 3/2015 | Gehl et al. |
| 2019/0046791 | A1 | 2/2019 | Ebbers et al. |
| 2019/0217080 | A1 | 7/2019 | Moss et al. |

OTHER PUBLICATIONS

Al-Habori, et al., Cell Volume and Ion Transport Regulation, Int. J. Biochem, vol. 26, No. 3, 1994, pp. 319-334.

Andre, et al., Gadolinium Blocks Membrane Permeabilization Induced by Nanosecond Electric Pulses and Reduces Cell Death, Bioelectrochemistry, vol. 79, No. 1, Aug. 2010, pp. 95-100.

Andreason, et al., Optimization of Electroporation for Transfection of Mammalian Cell Lines, Analytical Biochemistry, vol. 180, 1989, pp. 269-275.

Babiychuk, et al., Blebbing Confers Resistance against Cell Lysis, Cell Death and Differentiation, vol. 18, 2011, pp. 80-89.

Beebe, et al., Diverse Effects of Nanosecond Pulsed Electric Fields on Cells and Tissues, DNA and Cell Biology, vol. 22, No. 12, 2003, pp. 785-796.

Beebe, et al., Nanosecond Pulsed Electric Field (nsPEF) Effects on Cells and Tissues: Apoptosis Induction and Tumor Growth Inhibition, IEEE Transactions on Plasma Science, Mar. 2002, 6 pages.

Beebe, et al., Nanosecond Pulsed Electric Fields Modulate Cell Function through Intracellular Signal Transduction Mechanisms, Physiol. Meas., vol. 25, 2004, pp. 1077-1093.

Beebe, et al., Nanosecond, High-Intensity Pulsed Electric Fields Induce Apoptosis in Human Cells, The FASEB Journal, vol. 17, No. 11, Jun. 17, 2003, pp. 95-100.

Bevers, et al., Lipid Translocation Across the Plasma Membrane of Mammalian Cells, Biochimica et Biophysica Acta, vol. 1439, No. 3, Aug. 18, 1999, pp. 317-330.

Bier, et al., Kinetics of Sealing for Transient Electropores in Isolated Mammalian Skeletal Muscle Cells, Bioelectromagnetics, vol. 20, 1999, pp. 194-201.

Blachere, et al., Apoptotic Cells Deliver Processed Antigen to Dendritic Cells for Cross-Presentation, PLoS Biology, vol. 3, No. 6, Jun. 2005, pp. 1070-1078.

Bortner, et al., A Primary Role for $K^+$ and $Na^+$ Efflux in the Activation of Apoptosis, The Journal of Biological Chemistry, vol. 272, No. 51, Dec. 19, 1997, pp. 32436-32442.

Casares, et al., Caspase-Dependent Immunogenicity of Doxorubicin-Induced Tumor Cell Death, The Journal of Experimental Medicine, vol. 202, No. 12, 2005, pp. 1691-1701.

Casiano, et al., Distinct Cleavage Products of Nuclear Proteins in Apoptosis and Necrosis Revealed by Autoantibody Probes, Cell Death and Differentiation, vol. 5, 1998, pp. 183-190.

Charras, et al., Reassembly of Contractile Actin Cortex in Cell Blebs, The Journal of Cell Biology, vol. 175, No. 3, Nov. 6, 2006, pp. 477-490.

Chernomordik, et al., The Electrical Breakdown of Cell and Lipid Membranes: The Similarity of Phenomenologies, I Biochimica et Biophysica Acta, vol. 902, 1987, pp. 360-3730.

Chu, et al., Electroporation for the Efficient Transfection of Mammalian Cells with DNA, Nucleic Acids Research, vol. 15, No. 3, 1987, pp. 1311-1326.

Deng, et al., The Effects of Intense Submicrosecond Electrical Pulses on Cells, Biophysical Journal, vol. 84, Issue 4, Apr. 2003, pp. 2709-2714.

Deutsch, et al., Cell Volume Regulation in Lymphocytes, Renal Physiol Biochem, vol. 3, No. 5, 1988, pp. 260-276.

Dunn, et al., Low Temperature Selectively Inhibits Fusion between Pinocytic Vesicles and Lysosomes during Heterophagy of $^{125}I$-Asialofetuin by the Perfused Rat Liver, J. Biol Chem., vol. 255, No. 12, Jun. 25, 1980, pp. 5971-5978.

Escande-Geraud, et al., Reversible Plasma Membrane Ultrastructural Changes Correlated with Electropermeabilization in Chinese Hamster Ovary Cells, Biochimica et Biophysica Acta, vol. 939, 1988, pp. 247-259.

Galluzzi, et al., Essential Versus Accessory Aspects of Cell Death: Recommendations of the NCCD 2015, Cell Death and Differentiation, vol. 22, 2015, pp. 58-73.

Garon, et al., In Vitro and In Vivo Evaluation and a Case Report of Intense Nanosecond Pulsed Electric Field as a Local Therapy for Human Malignancies Int. J. Cancer, vol. 121, No. 3, Aug. 1, 2007, pp. 675-682.

Gehl, et al., Vascular Reactions to in Vivo Electroporation: Characterization and Consequences for Drug and Gene Delivery, Biochimica et Biophysica Acta, vol. 1569, 2002, pp. 51-58.

Glaser, et al., Reversible Electrical Breakdown of Lipid Bilayers: Formation and Evolution of Pores, Biochimicaa et Biophysica Acta, vol. 940, 1988, pp. 275-287.

Hall, et al., Nanosecond Pulsed Electric Fields (nsPEF) Induce Direct Electric Field Effects and Biological Effects on Human Colon Carcinoma Cells, DNA and Cell Biology, vol. 24, No. 5, 2005, pp. 283-291.

Haylett, et al., Endosome-Lysosome Fusion at Low Temperature, The Journal of Biological Chemistry, vol. 266, No. 13, 1991, pp. 8322-8327.

Hoffmann, et al., Sensors and Signal Transduction in the Activation of Cell Volume Regulatory Ion Transport Systems, Cell Volume Regulation, Contrib. Nephrol. Basel, Karger, vol. 123, 1998, pp. 50-78.

Ibey, et al., Dose-Dependent Thresholds of 10-ns. Electric Pulse Induced Plasma Membrane Disruption and Cytotoxicity in Multiple Cell Lines, PLoS ONE, vol. 6, No. 1, Jan. 2011, pp. 1-11.

Ibey, et al., Plasma Membrane Permeabilization by 60- and 600-ns Electric Pulses Is Determined by the Absorbed Dose, Bioelectromagnetics, vol. 30, No. 2, Feb. 2009, pp. 1-14.

Ibey, et al., Selective Cytotoxicity of Intense Nanosecond-Duration Electric Pulses in Mammalian Cells, Biochimica et Biophysica Acta, vol. 1800, No. 11, Nov. 2010, pp. 1-24.

(56) References Cited

OTHER PUBLICATIONS

Idone, et al., Repair of Injured Plasma Membrane by Rapid $Ca^{2+}$-Dependent Endocytosis, The Journal of Cell Biology, vol. 180, No. 5, Mar. 10, 2008, pp. 905-914.

Iitaka, et al., Blockade of Chloride Ion Transport Enhances the Cytocidal Effect of Hypotonic Solution in Gastric Cancer Cells, Journal of Surgical Research, vol. 176, 2012, pp. 524-534.

Jaiswal, et al., Membrane Proximal Lysosomes are the Major Vesicles Responsible for Calcium-Dependent Exocytosis in Nonsecretory Cells, The Journal of Cell Biology, vol. 159, No. 4, Nov. 25, 2002, pp. 625-635.

Kaufmann, et al., Specific Proteolytic Cleavage of Poly(ADP-ribose) Polymerase: An Early Marker of Chemotherapy-induced Apoptosis, Cancer Research, vol. 53, Sep. 1, 1993, pp. 3976-3985.

Kinosita, et al., Formation and Resealing of Pores of Controlled Sizes in Human Erythrocyte Membrane, Nature, vol. 268, Aug. 4, 1977, pp. 438-441.

Kinosita, et al., Hemolysis of Human Erythrocytes by a Transient Electric Field, Proc. Natl. Acad. Sci. USA, vol. 74, No. 5, May 1977, pp. 1923-1927.

Knight, et al., Calcium-Dependence of Catecholamine Release from Bovine Adrenal Medullary Cells after Exposure to Intense Electric Fields, J. Membrane Biol., vol. 68, 1982, pp. 107-140.

Kruman, et al., Calcium and Reactive Oxygen Species Mediate Staurosporine-Induced Mitochondrial Dysfunction and Apoptosis in PC12 Cells, Journal of Neuroscience Research, vol. 51, 1998, pp. 293-308.

Lariccia, et al., Massive Calcium-Activated Endocytosis without Involvement of Classical Endocytic Proteins, J. Gen. Physiol., vol. 137, No. 1, Jan. 2011, pp. 111-132.

Lee, et al., Kinetic Studies of Human Erythrocyte Membrane Resealing, Biochimica et Biophysica Acta, vol. 815, 1985, pp. 128-134.

Lee, et al., vol. Response of Quiescent and Interleukin 2-Stimulated T-Lymphocytes to Hypotonicity, Am J Physiol., vol. 254, No. 2, Feb. 1988, pp. C286-C296.

Liebert, et al., Dynamics of the Holes in Human Erythrocyte Membrane Ghosts, The Journal of biological Chemistry, vol. 257, No. 19, 1982, pp. 11660-11666.

Ma, et al., Therapy-Induced Microenvironmental Changes in Cancer, J Mol Med, vol. 94, 2016, pp. 497-508.

McNeil, et al., Loss, Restoration, and Maintenance of Plasma Membrane Integrity, The Journal of Cell Biology, vol. 137, No. 1, 1997, pp. 1-4.

Miyake, et al., Vesicle Accumulation and Exocytosis at Sites of Plasma Membrane Disruption, The Journal of Cell Biology, vol. 131, No. 6, Part 2, Dec. 1995, pp. 1737-1745.

Napotnik, et al., Nanosecond Electric Pulses Cause Mitochondrial Membrane Permeabilization in Jurkat Cells, Bioelectromagnetics, vol. 33, No. 3, 2012, pp. 257-264.

Nesin, et al., Manipulation of Cell Volume and Membrane Pore Comparison following Single Cell Permeabilization with 60- and 600-ns Electric Pulses, Biochimica et Biophysica Acta, vol. 1808, 2011, pp. 792-801.

Nuccitelli, et al. Optimized Nanosecond Pulsed Electric Field Therapy Can Cause Murine Malignant Melanomas to Self-Destruct with a Single Treatment, Int. J. Cancer., vol. 127, No. 7, Oct. 1, 2010, pp. 1727-1736.

Nuccitelli, et al., A New Pulsed Electric Field Therapy for Melanoma Disrupts the Tumor's Blood Supply and Causes Complete Remission Without Recurrence, Int. J. Cancer., vol. 125, No. 2, Jul. 15, 2009, pp. 438-445.

Nuccitelli, et al., First-in-Human Trial of Nanoelectroablation Therapy for Basal Cell Carcinoma: Proof of Method, Exp. Dermatol., vol. 23, No. 2, Feb. 2014, pp. 135-137.

Nuccitelli, et al., Nanoelectroablation of Murine Tumors Triggers a CD8-Dependent Inhibition of Secondary Tumor Growth, PLoS ONE, vol. 10, No. 7, Jul. 31, 2015, 17 pages.

Nuccitelli, et al., Nanosecond Pulsed Electric Fields Cause Melanomas to Self-Destruct, Biochemical and Biophysical Research Communications, vol. 343, No. 2, May 5, 2006, pp. 351-360.

Obeid, et al., Calreticulin Exposure is Required for the Immunogenicity of y-Irradiation and UVC Light-Induced Apoptosis , Cell Death and Differentiation, vol. 14, 2007, pp. 1848-1850.

Obeid, et al., Leveraging the Immune System during Chemotherapy: Moving Calreticulin to the Cell Surface Converts Apoptotic Death from "Silent" to Immunogenic, Cancer Res, vol. 67, No. 17, Sep. 1, 2007, pp. 7941-7944.

Okada, et al., Receptor-Mediated Control of Regulatory vol. Decrease (RVD) and Apoptotic Volume Decrease (AVD), Topical Review Journal of Physiology, vol. 532, No. 1, 2001, pp. 3-16.

Pahapill, et al., Modulation of Potassium Channels in Human T Lymphocytes: Effects of Temperature, Journal of Physiology, vol. 422, Mar. 1990, pp. 103-126.

Pakhomov, et al. Cancellation of Cellular Responses to Nanoelectroporation by Reversing the Stimulus Polarity, Cell Mol Life Sci., vol. 71, No. 22, Nov. 2014, pp. 4431-4441.

Pakhomov, et al., Characterization of the Cytotoxic Effect of High-Intensity, 10-ns Duration Electrical Pulses, IEEE Transactions on Plasma Science, vol. 32, No. 4, Aug. 2004, pp. 1579-1586.

Pakhomov, et al., Lipid Nanopores Can Form a Stable, Ion Channel-Like Conduction Pathway in Cell Membrane, Biochem Biophys Res Commun, vol. 385, No. 2, Jul. 24, 2009, pp. 1-13.

Pakhomov, et al., Long-Lasting Plasma Membrane Permeabilization in Mammalian Cells by Nanosecond Pulsed Electric Field (nsPEF), Bioelectromagnetics, vol. 28, No. 8, Dec. 2007, pp. 655-663.

Pakhomov, et al., Membrane Permeabilization and Cell Damage by Ultrashort Electric Field Shocks, Biochemistry and Biophysics, vol. 465, No. 1, Sep. 1, 2007, pp. 109-118.

Pakhomov, et al., Nanopores: A distinct Transmembrane Passageway in Electroporated Cells, Advanced Electroporation Techniques in Biology and Medicine, CRC Press, 2010, 20 pages.

Pakhomova, et al., Calcium-Mediated Pore Expansion and Cell Death Following Nanoelectroporation, Biochimica et Biophysica Acta, vol. 1838, No. 10, Oct. 2014, pp. 2547-2554.

Pakhomova, et al., Electroporation-Induced Electrosensitization, PLoS ONE, vol. 6, No. 2, Feb. 2011, pp. 1-10.

Pakhomova, et al., Two Modes of Cell Death Caused by Exposure to Nanosecond Pulsed Electric Field, PLoS ONE, vol. 8, No. 7, Jul. 23, 2013, pp. 1-10.

PCT/US2017/057698, "International Search Report" dated Feb. 27, 2018, 5 pages.

Potter, Application of Electroporation in Recombinant DNA Technology, Methods Enzymology, vol. 217, No. 148, 1993, pp. 461-478.

Rassokhin, et al., Cellular Regulation of Extension and Retraction of Pseudopod-like Blebs Produced by Nanosecond Pulsed Electric Field (nsPEF), Cell Biochem Biophys, vol. 69, No. 3, Jul. 2014, pp. 555-566.

Rassokhin, et al., Electric Field Exposure Triggers and Guides Formation of Pseudopod-Like Blebs in U937 Monocytes, J. Membr. Biol., vol. 245, No. 9, Sep. 2012, pp. 521-529.

Ren, et al., An Apoptosis Targeted Stimulus with Nanosecond Pulsed Electric Fields (nsPEFs) in E4 Squamous Cell Carcinoma, Apoptosis, vol. 16, 2011, pp. 382-393.

Ren, et al., Nanosecond Pulsed Electric Fields (nsPEFS) Activate Intrinsic Caspase-Dependent and Caspase-Independent Cell Death in Jurkat Cells, Biochemical and Biophysical Research Communications, vol. 421, No. 4, May 18, 2012, pp. 808-812.

Rizzuto, et al., Microdomains of Intracellular $Ca^{2+}$: Molecular Determinants and Functional Consequences, Physiol. Rev., vol. 86, 2006, pp. 369-408.

Rols, et al., Control of Electric Field Induced Cell Membrane Permeabilization by Membrane Order, Biochemistry, vol. 29, 1990, pp. 2960-2966.

Rols, et al., Temperature Effects on Electrotransfection of Mammalian Cells, Nucleic Acids Research, vol. 22, No. 3 Feb. 11, 1994, p. 540.

Saulis, Cell Electroporation: Estimation of the Number of Pores and Their Sizes, ISA, 1999, pp. 291-296.

(56) References Cited

OTHER PUBLICATIONS

Saulis, et al., Determination of Cell Electroporation from the Release of Intracellular Potassium Ions, Analytical Biochemistry, vol. 360, 2007, pp. 273-281.

Saulis, et al., Kinetics of Pore Resealing in Cell Membranes After Electroporation, Bioelectrochemistry and Bioenergetics, Journal of Electroanalytical Chemistry and Interfacial Electrochemistry, vol. 321, Issue 1, Aug. 1991, pp. 1-13.

Saulis, The Loading of Human Erythrocytes With Small Molecules by Electroporation, Cellular & Molecular Biology Letters, vol. 10, 2005, pp. 23-35.

Savitskaya, et al. Mechanisms of Apoptosis, Biochemistry, vol. 80, No. 11, 2015, pp. 1393-1405.

Schoenbach, et al., Bioelectric Effects of Intense Nanosecond Pulses, IEEE Transactions on Dielectrics and Electrical Insulation, vol. 14, No. 5, Oct. 2007, pp. 1088-1109.

Semenov, et al., Primary Pathways of Intracellular $Ca^{2+}$ Mobilization by Nanosecond Pulsed Electric Field, Biochim. Biophys. Acta, vol. 1828, No. 3, Mar. 2013, pp. 981-989.

Semenov, et al., Recruitment of the Intracellular $Ca^{2+}$ By Ultrashort Electric Stimuli: the Impact of Pulse Duration, Cell Calcium, vol. 54, No. 3, Sep. 2013, pp. 145-150.

Serpersu, et al., Reversible and Irreversible Modification of Erythrocyte Membrane Permeability by Electric Field, Biochimica et Biophysica Acta, vol. 812, 1985, pp. 779-785.

Sowers, et al., Electropore Diameters, Lifetimes, Numbers, and Locations in Individual Erythrocyte Ghosts, FEBS Letters, vol. 205, No. 2, Sep. 1986, 6 pages.

Stacey, et al., Differential Effects in Cells Exposed to Ultra-Short, High Intensity Electric Fields: Cell Survival, DNA Damage, and Cell Cycle Analysis, Mutation Research, 2003, vol. 542, pp. 65-75.

Tam, et al., Exocytosis Of Acid Sphingomyelinase by Wounded Cells Promotes Endocytosis and Plasma Membrane Repair, The Journal of Cell Biology, vol. 189, No. 6 Jun. 7, 2010, pp. 1027-1038.

Tang et al. "Diode Opening Switch Based Nanosecond High Voltage Pulse Generators for Biological and Medical Applications", IEEE Transactions on Dielectrics and Electrical Insulation, vol. 14, No. 4, 2007, pp. 878-883.

Teissie, et al., Correlation Between Electric Field Pulse Induced Long-Lived Permeabilization and Fusogenicity in Cell Membranes, Biophysical Journal, Apr. 1998, vol. 74, pp. 1889-1898.

Teissie, et al., Evidence of Voltage-Induced Channel Opening in Na/k ATpase of Human Erythrocyte Membrane, J. Membrane Biol., vol. 55, 1980, pp. 133-140.

Thompson, et al., Permeabilization of the Nuclear Envelope following Nanosecond Pulsed Electric Field Exposure, Biochemical and Biophysical Research Communications, vol. 470, 2016, pp. 35-40.

Tombal, et al., Assessment and Validation of a Microinjection Method for Kinetic Analysis of $[Ca^{2+}]i$ in Individual Cells Undergoing Apoptosis, Cell Calcium, vol. 25, No. 1, 1999, pp. 19-28.

Vernier, et al., Calcium Bursts Induced by Nanosecond Electric Pulses, Biochemical and Biophysical Research Communications, vol. 310, No. 2, Oct. 17, 2003, pp. 286-295.

Vernier, et al., Nanoelectropulse-Driven Membrane Perturbation and Small Molecule Permeabilization, BMC Cell Biology, 2006, pp. 1-16.

Vernier, et al., Nanoelectropulse-Induced Phosphatidylserine Translocation, Biophysical Journal, vol. 86, Jun. 2004, pp. 4040-4048.

Walker, et al., Oxygen Enhances Lethal Effect of High-Intensity, Ultrashort Electrical Pulses, Bioelectromagnetics, vol. 27, Apr. 2006, pp. 221-225.

Wang, et al. "Solid-State High Voltage Nanosecond Pulse Generator," IEEE Pulsed Power Conference, 2005, pp. 1199-1202.

Wang, et al., Synergistic Effects of Nanosecond Pulsed Electric Fields Combined with Low Concentration of Gemcitabine on Human Oral Squamous Cell Carcinoma In Vitro, Plos One, vol. 7, Issue 8, e43213, Aug. 2012, 9 pages.

White, et al., Stimulation of Capacitative Calcium Entry in HL-60 Cells by Nanosecond Pulsed Electric Fields, The Journal of Biological Chemistry, vol. 279, No. 22, May 28, 2004, pp. 22964-22972.

Yang, et al., Differential Sensitivities of Malignant and Normal Skin Cells to Nanosecond Pulsed Electric Fields, Technology in Cancer Research and Treatment, vol. 10, No. 3, Jun. 2011, pp. 281-286.

Yin, et al., Cutaneous Papilloma and Squamous Cell Carcinoma Therapy Utilizing Nanosecond Pulsed Electric Fields (nsPEF), PLoS ONE, vol. 7, No. 8, Aug. 28, 2012, pp. 1-11.

Zhao, et al., Level of Expression of Phospholipid Scramblase Regulates Induced Movement of Phosphatidylserine to the Cell Surface, The Journal of Biological Chemistry, vol. 273, No. 12, 1998, pp. 6603-6606.

Zitvogel, et al., Immunogenic Tumor Cell Death for Optimal Anticancer Therapy: The Calreticulin Exposure Pathway, Clinical Cancer Research, vol. 16, No. 12, Jun. 15, 2010, pp. 3100-3104.

PCT/US2017/057698, Preliminary Report on Patentability dated May 2, 2019, 6 pages.

Kanduser et al., "The temperature effect during pulse application on cell membrane fluidity and permeabilization," Bioelectrochemistry, 2008, vol. 74, pp. 52-57.

\* cited by examiner

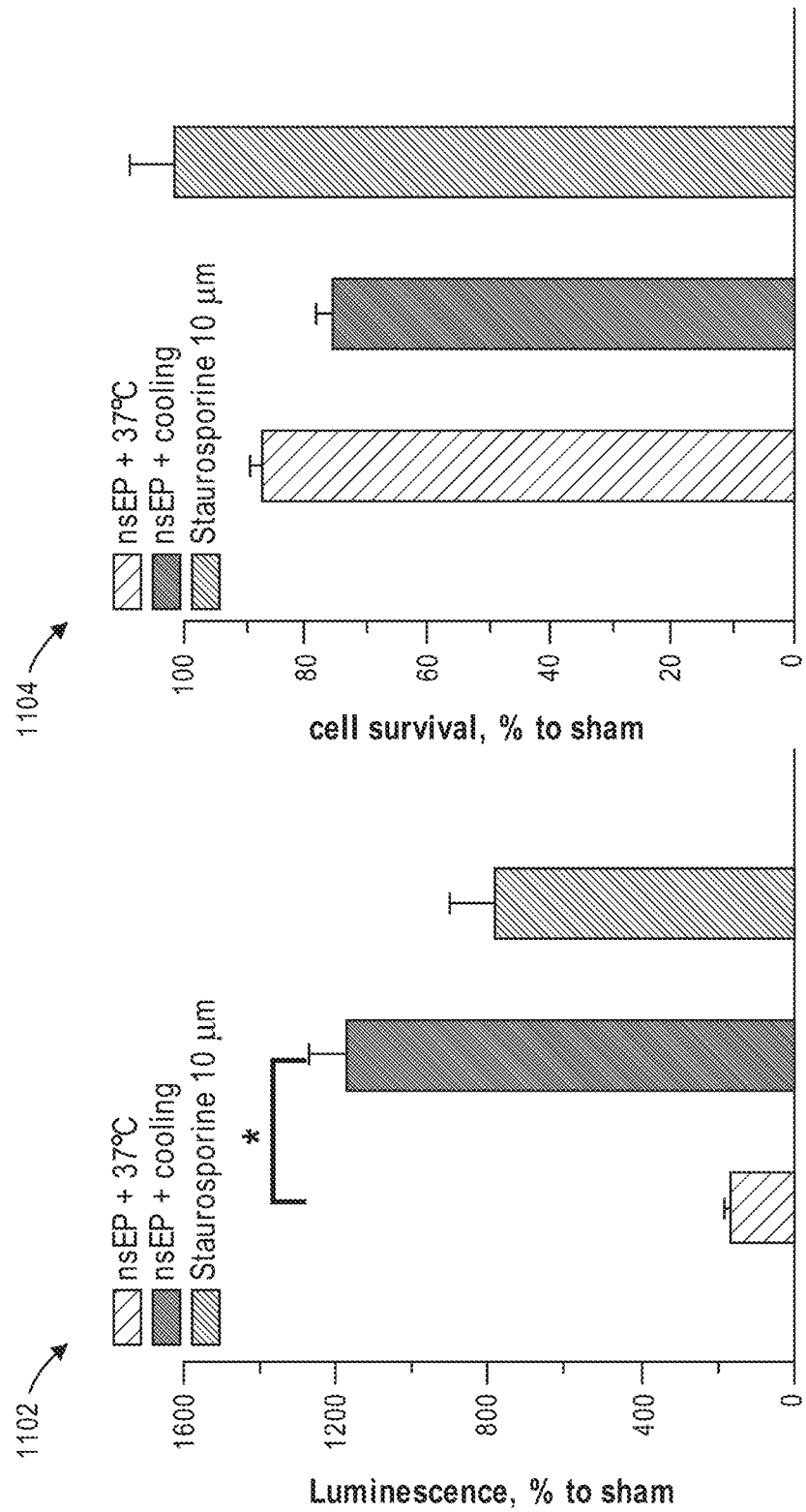

METHODS AND DEVICES FOR USING SUB-MICROSECOND ELECTRIC PULSES TO TRIGGER APOPTOSIS

CROSS-REFERENCES TO RELATED APPLICATIONS

The present application is a non-provisional application that claims the benefit and priority under 35 U.S.C. § 119(e) of U.S. Provisional Application No. 62/410,782, filed Oct. 20, 2016, entitled "THE CYTOTOXIC SYNERGY OF NANOSECOND ELECTRIC PULSES AND LOW TEMPERATURE LEADS TO APOPTOSIS," and U.S. Provisional Application No. 62/417,498, filed Nov. 4, 2016, entitled "THE CYTOTOXIC SYNERGY OF NANOSECOND ELECTRIC PULSES AND LOW TEMPERATURE LEADS TO APOPTOSIS." The entire contents of each of these applications are hereby incorporated by reference for all purposes.

STATEMENT AS TO RIGHTS TO INVENTIONS MADE UNDER FEDERALLY SPONSORED RESEARCH OR DEVELOPMENT

This invention was made with government support under Grant No. R01 GM088303 awarded by the National Institute of Health and Grant No. FA9559-15-1-0517 awarded by the Air Force. The government has certain rights in the invention.

BACKGROUND

Ablation refers to a wide variety of minimally invasive surgical methods used to treat and remove tumors and other abnormal growth, for example, cancerous tumors. Ablation often involves heating, vaporization, chipping, or other erosive processes that are used to slowly remove the tumor in a controlled manner. For example, special probes or electrodes are often used (e.g., to emit radio frequency waves) in order to "burn" and remove the tumors.

An emerging modality for tumor ablation is electroporation using ultra-short, high-field strength electric pulses. In this approach, a generator is used to create high amplitude electric pulses of very short duration (e.g., less than 1 microsecond) that are applied to the tumor using electrodes. The electric pulses induce a voltage across the cell membranes of the tumor cells which leads to opening of pores in the cell membranes, either temporarily or permanently. Using the pulses to open pores in the cell membrane of the tumor cells may ultimately trigger apoptosis (i.e. programmed cell death) and the death of the tumor cells. For a detailed discussion of such applications, for example, see, Garon et al. "In Vitro and In Vivo Evaluation and a Case Report of Intense Nanosecond Pulsed Electric Field as a Local Therapy for Human Malignancies", Int. J. Cancer, vol. 121, 2007, pages 675-682. The entire content of this publication is incorporated herein by reference.

However, this approach requires a great deal of power and large equipment in order to generate the ultra-short, high-field strength electric pulses needed to trigger apoptosis. Accordingly, there exists a need for improvements to the electroporation process that improve ablation efficiency.

SUMMARY

The present disclosure generally relates to methods of using nanosecond electric pulses (nsEP) and nanosecond pulsed electric fields (nsPEF) to trigger apoptosis of biological cells for tissue ablation, as well as ways to more efficiently trigger apoptosis when employing nsEP/nsPEF. The methods of the present disclosure enable achieving an ablation of similar efficiency and similar results with less power needed, using, for example, lower strength electric pulses or a reduced number of electric pulses, which can be produced with less bulky equipment.

In some embodiments, the method may include applying an electrode to an abnormal growth of a subject, with the electrode being electrically coupled to a generator. The generator produces sub-microsecond electric pulses that have a width of between 1 ns and 1000 ns. The electrode conducts these sub-microsecond electric pulses to the abnormal growth to allow an electric field (based on the sub-microsecond electric pulses) to be pulsed through the abnormal growth for a first duration. This electric field may have an intensity of more than 1 kV/cm.

The method includes cooling the abnormal growth for a second duration. Pulsing the electric field through the abnormal growth and cooling the abnormal growth, done together, may synergistically stimulate apoptosis of cells in the abnormal growth. This method can be performed on human subjects, as well as other mammal and animal subjects. The abnormal growth can be a tumor that is cancerous or noncancerous, such as a malignant tumor, a pre-malignant tumor, or a benign tumor.

In some embodiments, the intensity of the electric field may be sufficient to trigger apoptosis of cells in the abnormal growth (e.g., by opening pores in the cellular membranes of the cells of the abnormal growth), and the electric field may be able to trigger apoptosis without the cooling step. However, the additional cooling of the abnormal growth according to the methodology of the present disclosure may prolong a permeabilized state of the cellular membranes of cells of the abnormal growth (e.g., caused by pulsing the electric field through the abnormal growth). This, in turn, may lead to decrease of the cell survival rate, allowing, for example, for similar levels of apoptosis to be achieved with lower electric field intensity. Thus, the intensity of the electric field can be reduced compared to a level of intensity of the electric field otherwise required to trigger the apoptosis without the cooling step.

In various embodiments, the cooling step may be performed until the temperature of the abnormal growth is lowered to be between zero degrees Celsius and twenty degrees Celsius, for example, to approximately two degrees Celsius. This reduction in temperature may inhibit resealing of pores opened by the electric pulses. The cooling step may be performed in various ways, which include, for example, applying an ice-pack to the abnormal growth, or via perfusion by injecting saline into the subject (e.g., at or around the abnormal growth). Refrigeration of the tumor can be achieved also by cooling the nsEP-delivering electrodes.

In various embodiments, the second duration (when the abnormal growth is cooled) can be at least five minutes. In certain embodiments, the second duration can be under one hour, or approximately between fifteen and thirty minutes. Cooling the abnormal growth for the second duration can occur, for example, immediately following the first duration, or it may occur at least in part during the first duration (when the electric field is pulsed through the abnormal growth). In various embodiments, the intensity of the electric field can be between 0.5-70 kV/cm, or the intensity of the electric field can be between 5-7 kV/cm. In various embodiments, the sub-microsecond electric pulses are pulsed at a frequency of 100 Hz.

As a result of these steps and configurations, the synergistic stimulation of apoptosis caused by the pulsing and cooling steps may result in at least 25% reduction in ablated tissue cell survival as compared to the cell survival rate of ablated tissue subjected to pulsing alone without cooling. Thus, the synergy of the pulsing and cooling steps may provide substantially the same ablation efficiency while allowing one or more of the following: 1) lowering pulse voltage, 2) lowering pulse numbers, or 3) increasing a distance between electrodes. The synergy of the pulsing and cooling steps may also minimize the side effects of ablation.

In some embodiments, the method of tissue ablation may include applying a plurality of nanosecond electric field pulses to the tissue located on, or in, a subject. The plurality of nanosecond electric field pulses may have an intensity of greater than 1,000 V/cm, which is sufficient to open pores in cell membranes of the tissue. With the pores in the cell membranes opened, the tissue may be cooled such that the pores opened by the electric field pulses seal up slower than if no cooling had occurred.

In various embodiments, performing both the steps of applying the plurality of pulses and cooling may synergistically stimulate apoptosis of cells in the tissue, resulting in at least a 25% reduction in survival of the cells in the tissue, as compared to survival of the cells in the tissue in a comparable application of the plurality of nanosecond electric field pulses performed without cooling the tissue. In some cases, the reduction in survival of cells in the tissue may be more drastic, such as a 25% to 80% reduction in survival of the cells in the tissue, as compared to survival of the cells in the tissue in the comparable application of the plurality of nanosecond electric field pulses performed without cooling the tissue. In various embodiments, the intensity of the plurality of electric field pulses is not at a level sufficient to cause necrosis.

In various embodiments, cooling the tissue prolongs a permeabilized state of the cell membranes. The intensity of the plurality of electric field pulses may be reduced compared to a level of intensity of the electric field pulses otherwise required to trigger the apoptosis without the cooling.

In various embodiments, cooling the tissue may involve lowering a temperature of the tissue to be between zero degrees Celsius and twenty degrees Celsius, or to approximately two degrees Celsius. This reduction in temperature may inhibit resealing of the pores opened by the plurality of electric field pulses. The cooling may be performed at least partly concurrent with the application of the plurality of nanosecond electric field pulses (e.g., the nanosecond electric field pulses are applied for a first duration, the cooling is performed for a second duration, and the first and the second durations at least partially overlap).

Devices and systems for use in the methods of the present disclosure are also provided. Reference to the remaining portions of the specification, including the drawings and claims, will realize other features and advantages of the present disclosure. Further features and advantages, as well as the structure and operation of various embodiments, are described in detail below with respect to the accompanying drawings. In the drawings, like reference numbers indicate identical or functionally similar elements.

BRIEF DESCRIPTION OF THE DRAWINGS

FIGS. 11A-11D illustrate graphs depicting how cooling of nsEP-exposed cells induces caspase 3/7 activation and PARP cleavage, in accordance with embodiments of the present disclosure.

DETAILED DESCRIPTION

Figure 1:
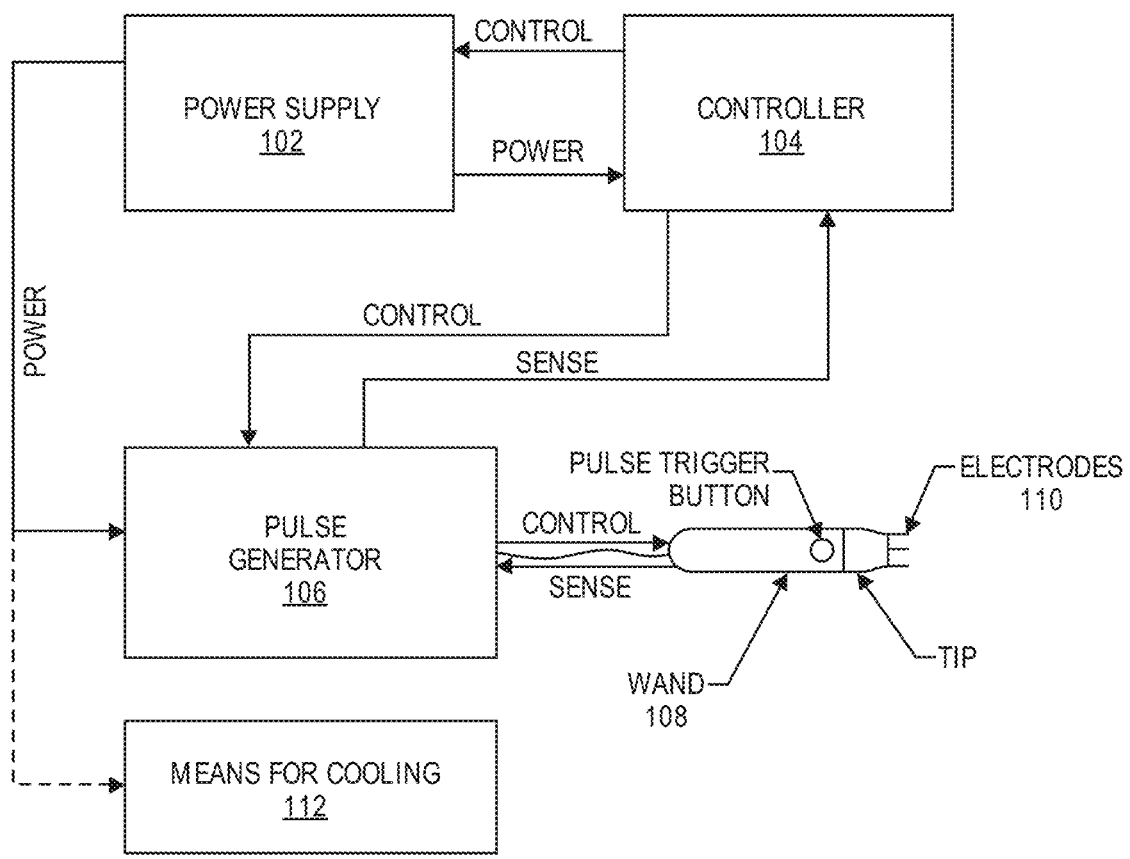
FIG. 1 illustrates schematically a system for generating and delivering nanosecond electrical pulses, in accordance with embodiments of the present disclosure.

In the following detailed description, reference is made to the accompanying drawings that show, by way of illustration, some examples of embodiments in which the disclosure may be practiced. With reference to the above-listed drawings, this section describes particular embodiments and their detailed construction and operation. The embodiments described herein are set forth by way of illustration only and not limitation. Those skilled in the art will recognize in light of the teachings herein that, for example, other embodiments are possible, variations can be made to the example embodiments described herein, and there may be equivalents to the components, parts, or steps that make up the described embodiments.

Terms. A "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a pre-malignant tumor is precancerous, and a benign tumor is noncancerous. Thus, an abnormal, uncontrolled growth of tissue, may include those that are cancerous, precancerous, and benign. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus. Other examples of tumors or abnormal growth include adipose tissue or fat, warts, calluses, corns, skin lesions, and other types of unwanted cosmetic/dermal growths.

"Apoptosis" of a tumor or cell includes an orderly, programmed cell death, or as otherwise known in the art.

A "nanosecond electric pulse" or a "sub-microsecond electric pulse", sometimes abbreviated as nsEP, refers to an electrical pulse with a width of between 0.1 nanoseconds (ns) to 1000 nanoseconds, or as otherwise known in the art. A plurality of nanosecond electric pulses may be used to generate a nanosecond pulsed electric field.

A "nanosecond pulsed electric field", sometimes abbreviated as nsPEF, includes an electric field with a pulse width of between 0.1 nanoseconds (ns) to 1000 nanoseconds, or as otherwise known in the art. It is sometimes referred to as sub-microsecond pulsed electric field. NsPEFs often have high peak voltages, such as 10 kilovolts per centimeter (kV/cm), 20 kV/cm, to 500 kV/cm. NsPEFs have been found to trigger both necrosis and apoptosis in cancerous tumors. Selective treatment of such tumors with nsPEFs can induce apoptosis within the tumor cells without substantially affecting normal cells in the surrounding tissue due to its non-thermal nature. Treatment of biological cells with nsPEF often uses a multitude of periodic pulses at a frequency ranging from 0.1 per second (Hz) to 10,000 Hz.

A temperature of "about" or "approximately" a certain number of degrees includes temperatures with within a fixed tolerance, such as 0.1, ±0.2, ±0.3, ±0.4, ±0.5, ±0.7, ±1.0, or ±2.0 degrees, or other tolerances as acceptable in the art.

A time of "about" or "approximately" a certain number of nanoseconds includes times within a tolerance of ±1%, 2%, 3%, 4%, 5%, 7.5%, 10%, 15%, 20%, 25% or other percentages, or fixed tolerances, such as ±0.1, ±0.2, ±0.3, ±0.4, ±0.5, ±0.7, ±1.0, ±2.0, ±3.0, ±4.0 ±5.0, ±7.0, ±10, ±15, ±20, ±25, ±30, ±40, ±50, ±75 ns, or other tolerances as acceptable in the art in conformance with the effectivity of the time period. Similar, a duration may be within a certain time if it is within a tolerance of ±1%, 2%, 3%, 4%, 5%, 7.5%, 10%, 15%, 20%, 25% or other percentages, or fixed tolerances, such as ±0.1, ±0.2, ±0.3, ±0.4, ±0.5, ±0.7, ±1.0, ±2.0, ±3.0, ±4.0 ±5.0, ±7.0, ±10, ±15, ±20, ±25, ±30, ±40, ±50, ±75 ns, or other tolerances as acceptable in the art in conformance with the effectivity of the time period. For instance, in some cases, a duration of fourteen minutes and fourty-five seconds may be considered approximately similar or equivalent to a duration of fifteen minutes.

Introduction

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

Ultra-short duration, high-field strength electric pulses, such as nanosecond electric pulses (nsEP) with a duration of 1,000 nanoseconds (ns) or less, have been recently proposed as a new local and minimally invasive modality to treat tumors. The advantages of nsEP over other ablation methods include preservation of the extracellular matrix and reduced collateral damage to healthy tissue; relative simplicity of the treatment; and fast recovery. NsEP can be used to open pores in the cell membranes of tumor cells, which may ultimately trigger apoptosis of those cells.

However, cooling the tumor cells may counteract cell self-repair mechanisms to keep those pores (opened via nsEP) opened longer. The combined application of nsEP and the cooling of tissue may have synergistic effects on promoting apoptosis the tumor cells. The increased ablation efficiency that is attained can be utilized in many practical ways. For instance, the generation of nsEP may require large devices drawing a large amount of power to produce the pulses. Gains in ablation efficiency provided by the combined application of nsEP and the cooling of tissue provide important benefits of using lower number of pulses or lower pulse strength, which can be provided by smaller pulse generators operating on less power. In addition, one major obstacle to a wider use of nsEP in the clinic is the limited output voltage of the existing pulse generators, which limits the size of the ablation zone thus requiring multiple electrode insertions and exposures when treating bigger tumors. Methodology and devices of the present disclosure solves the issues associated with this major obstacle by eliminating or reducing multiple electrode insertions.

One such system that can utilize the combined application of nsEP and the cooling of tissue in order to eliminate or reducing multiple electrode insertions, or to provide similar ablation results with reduced pulse parameters, is shown in FIG. 1. FIG. 1 illustrates a system for generating and delivering electrical sub-microsecond (e.g., nanosecond) duration pulses.

In some embodiments, the system may include a power supply 102, a controller 104, a pulse generator 106, a wand 108 having one or more electrodes 110, and/or a means for cooling 112. The power supply 102 may supply power to the controller 104 and the pulse generator 106. Optionally, in some embodiments, the power supply 102 may also supply power to the means for cooling 112.

The pulse generator 106 may generate electrical pulses which are conducted by the electrodes 110 of the wand 108. The electrodes 110 of the wand 108 may be applied to tissue of a subject in order to pulse an electric field through the tissue. The means for cooling 112 may be used to cool the tissue. In some embodiments, the means for cooling 112 may be an ice pack or a cooling pack that is configured to applied to tissue in order to lower the temperature of the tissue.

Figure 2:
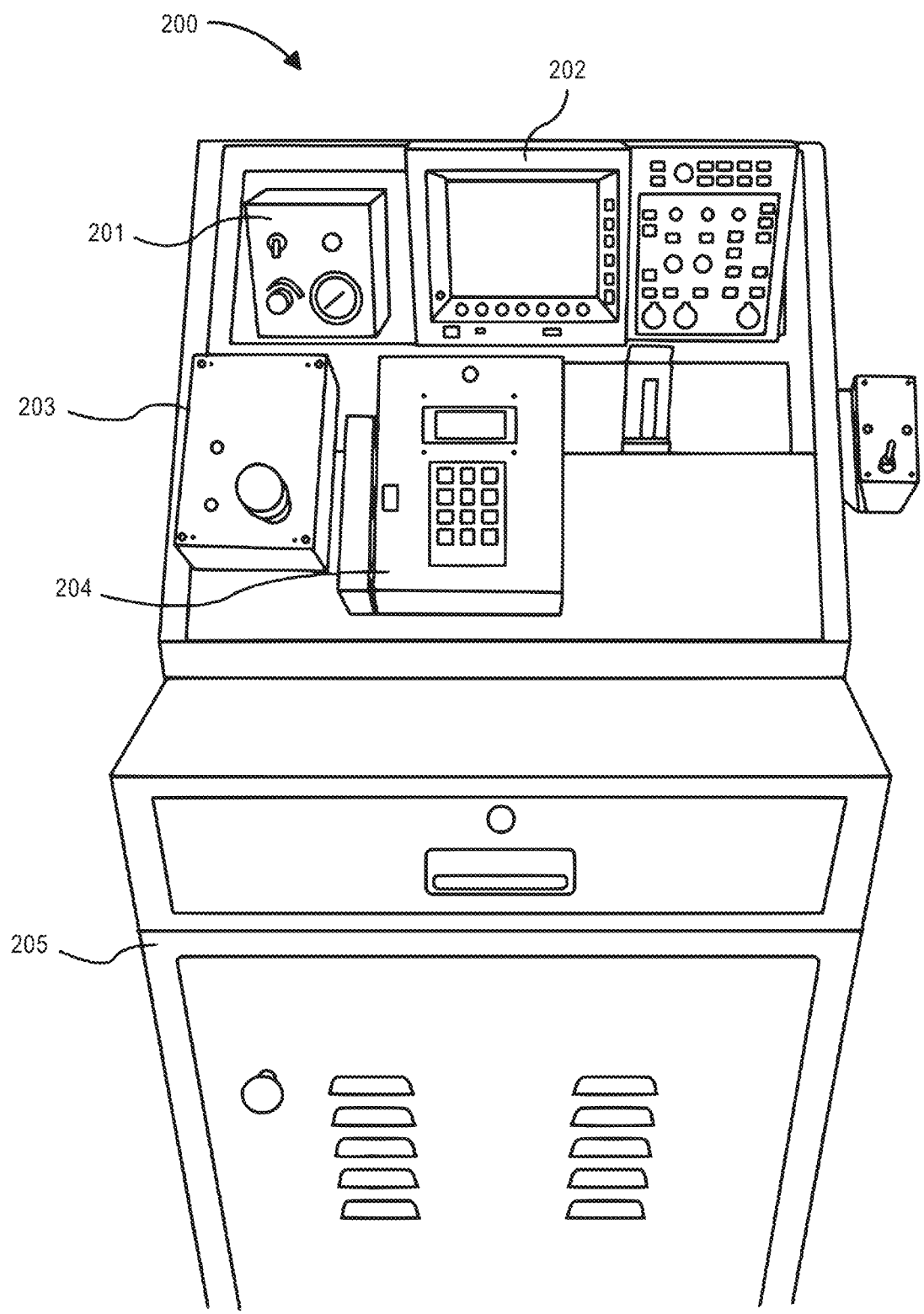
FIG. 2 illustrates an example of a nanosecond pulse generator, in accordance with embodiments of the present disclosure.

FIG. 2 illustrates a nanosecond pulse generator, in accordance with embodiments of the present disclosure. The nanosecond pulse generator 200, which represents an example of an embodiment of the pulse generator 106 described in regards to FIG. 1, may generate electrical pulses of sub-microsecond duration with the electrical pulses having variably configurable parameters. For instance, the nanosecond pulse generator 200 may be capable of changing pulse widths, duty cycles, and other pulse parameters for the generated electrical pulses. In some embodiments, pulse widths, duty cycles, and other pulse parameters are controlled by a spark gap, the critical distance of which is controlled by compressed gas, such as compressed carbon dioxide.

In some embodiments, the nanosecond pulse generator 200 may include pressure readout 201, digitizing oscilloscope 202, emergency off button 203, and microcontroller interface 204. These components may all be connected to the nanaosecond pulse generator 200 within a metal-shielded cabinet 205.

A human operator may input a number of pulses, amplitude, and frequency into a numeric keypad of the microcontroller interface 204. In some embodiments, the pulse width is fixed. A microcontroller of the nanosecond pulse generator 200 sends signals to a high voltage power supply (HVPS) and pressure system to control a spark gap (switch) within the cabinet 205. Fiber optic cables electrically isolate the contents of the metal cabinet with the nanosecond pulse generator 200, the high voltage circuit, from the outside. In order to further isolate the generator, the nanosecond pulse generator 200 may be battery powered instead of from a wall outlet.

Other examples of high voltage pulse generators, besides the nanosecond pulse generator 200 shown in the figure, can be seen in: Gundersen et al. "Nanosecond Pulse Generator Using a Fast Recovery Diode", IEEE 26.sup.th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Schoenbach et al. "Method and Apparatus for Intracellular Electro-Manipulation", U.S. Pat. No. 6,326,177; Gundersen et al., "Method for Intracellular Modifications Within Living Cells Using Pulsed Electric Fields", U.S. Patent Application No. 2006/0062074; Kuthi et al., "High Voltage Nanosecond Pulse Generator Using Fast Recovery Diodes for Cell Electro-Manipulation", U.S. Pat. No. 7,767,433; Krishnaswamy et al., "Compact Subnanosecond High Voltage Pulse Generation System for Cell Electro-Manipulation", U.S. Patent Application No. 2008/0231337; and Sanders et al. "Nanosecond Pulse Generator", U.S. Patent Application No. 2010/0038971. The entire content of these publications is incorporated herein by reference.

Figure 3:
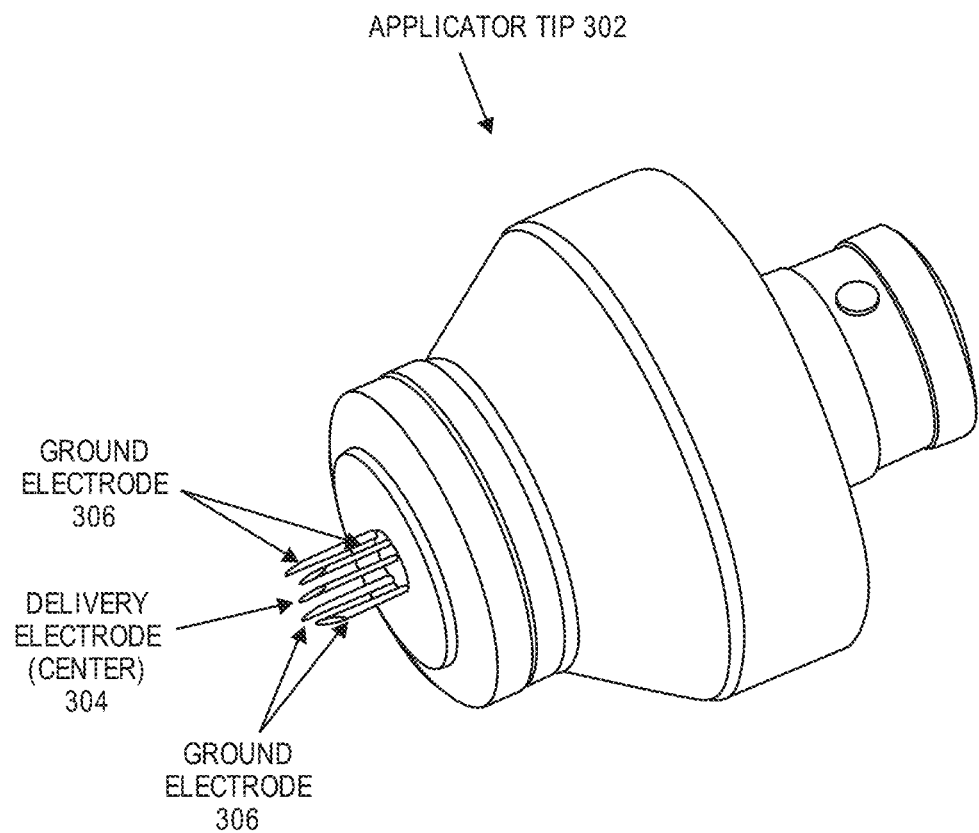
FIG. 3 illustrates a perspective view of an applicator tip with electrodes, in accordance with embodiments of the present disclosure.

FIG. 3 illustrates a perspective view of an example of an applicator tip with electrodes, which may be used in various embodiments of the present disclosure. In particular, an applicator tip 302 is shown that has one delivery electrode 304 and four ground electrodes 306 surrounding the delivery electrode 304.

The nanosecond electrical pulses produced by a generator can be delivered to tissue by using applicator tip 302 (e.g., on a wand, such as the wand 108 shown in FIG. 1. In some embodiments, each electrode may be constructed by using a 30 gauge needle (i.e. about 0.255 mm in diameter). In some embodiments, the delivery electrode 304 and the ground electrodes 306 may have the same length for each applicator tip 302. This length may vary in the range of about 2 millimeters (mm) to 5 mm. The electrodes may be placed to form a square pattern, with the ground electrodes 306 at the corners of this square and the delivery electrode 304 at its center. Center-to-center distance between the delivery electrode 304 and each of the ground electrodes 306 may be about 1.75 mm. This configuration provides a volume of about 30.625 cubic-millimeters (mm3) within the boundary formed by the ground electrodes 306. In some embodiments, the ground electrodes 306 and the delivery electrode 304 may be electrically isolated from each other by embedding them in a Teflon insulation (not shown in FIG. 3).

The tip configuration may be different than illustrated. There may be other applicator tip configurations suitable for applying electrical pulses to tissue. These configurations may include tips comprising at least one delivery electrode and at least one ground electrode. For example, as the system disclosed above is coaxial in nature, with the ground electrodes surrounding the delivery electrode, any number of needle configurations may be realized, including a circular arrangement with five or more ground electrodes, a triangular arrangement with three ground electrodes, wherein the delivery electrode may be placed at the geometrical center of such arrangements. A simple linear arrangement with just two opposing electrodes, i.e., one return electrode and one delivery electrode, may also be used for the delivery of the electrical pulses.

Still other tip configurations, for example those with different electrode spacing or length, may also be used for the delivery of electrical pulses to tissue. However, as the effect of these short pulses on cells is largely dependent upon the strength of electric field, an increase in return and active electrode spacing may have to be accompanied by a proportional increase in output voltage to maintain the required field for the effect on cells. Similarly, if the spacing is reduced, the voltage could be proportionally decreased.

Figure 4:
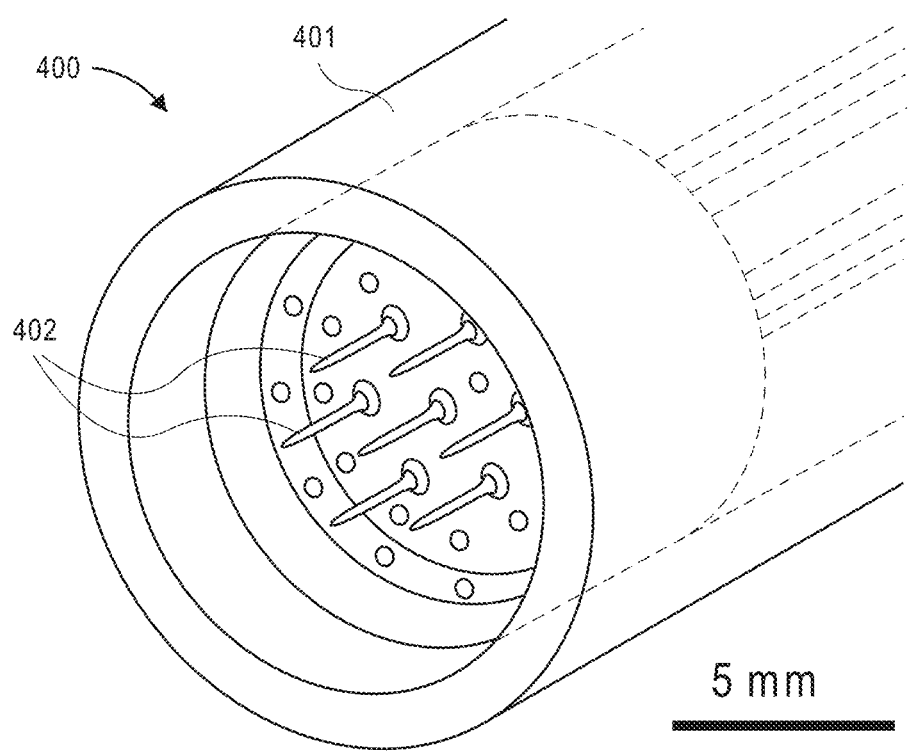
FIG. 4 illustrates a perspective view of an example electrode, in accordance with embodiments of the present disclosure.

FIG. 4 illustrates a perspective view of an example electrode, in accordance with embodiments of the present disclosure. In particular, the figure shows a seven-needle suction electrode 400. In electrode 400, the sheath 401 surrounds seven sharp needle electrodes 402 with an broad opening at a distal end. When the open, distal end is placed against tissue, air is evacuated from the resulting chamber sufficient to draw tissue (e.g., the entire tumor or a portion thereof) into the chamber. The tumor is drawn so that one or more of the needle electrodes 402 preferably penetrates the tumor. The needle electrodes 402 may be configured to pierce the tumor. The center needle is at one polarity, and the outer six needles are at the opposite polarity. An electric field can then be precisely applied to the tumor using the electrode 400 to conduct the electric pulses produged by the generator, such as generator 200 shown in FIG. 2.

The needle electrodes 402 can be apposed, one of each positive and negative pair of electrodes on one side of a tumor and the other electrode of the pair on an opposing side of the tumor. Opposing sides of a tumor can include areas outside or within a tumor, such as if a needle electrode 402 pierces a portion of the tumor.

It should be noted that this is only an example configuration of the electrode. The nature of the electrode used mainly depends upon the shape of the tumor or other abnormal growth. Its physical size and stiffness can also be taken into account in selection of a particular electrode type.

Figure 5:
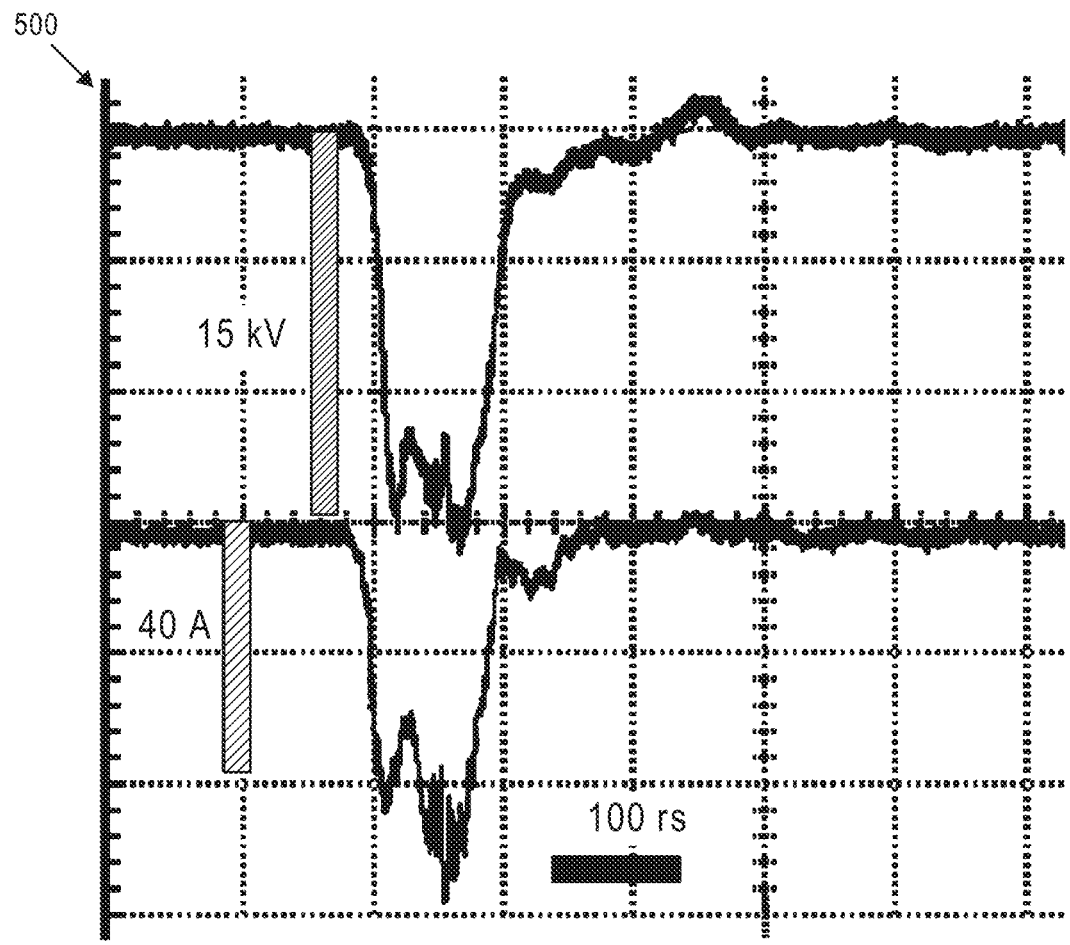
FIG. 5 illustrates an example profile (e.g., voltage and current) of an electrical pulse, in accordance with embodiments of the present disclosure.

FIG. 5 illustrates a pulse profile 500 of an electric pulse in accordance with an embodiment. Output from the spark gap is shown with voltage on the top of the figure and amperage on the bottom for a single pulse. As shown, the pulse has an amplitude of about 12 kV and an amperage of about 60 A, which lasts for approximately 100 ns. Thus, twelve kilovolts was applied to suction electrodes with 4 mm between the plates so that the tumors experienced 30 kV/cm, and current varied between 12 and 60 A. Given a voltage, current depends heavily on the electrode type and skin resistance. Other examples of a nanosecond electric pulse, as applied to biological cells, are shown and described in U.S. Pat. No. 6,326,177 (to Schoenbach et al.), which is incorporated herein by reference in its entirety for all purposes.

In some embodiments, the pulse duration may be at least 0.01 nanoseconds (ns), and in some embodiments it may be measured at the full-width-half-maximum (FWHM). The pulse duration may also be at least 1 ns, or at least 5 ns The pulse duration may be 1,000 ns or shorter. In some embodiments, the duration of the pulse (e.g., at FWHM) may be in the range of 0.01 ns to 1,000 ns. The duration of the pulse may also be in the range of 1 ns to 100 ns, or in the range of 1 ns to 30 ns.

In some embodiments, the applied electrical energy per volume of tissue may also be in the range of 0.10 mJ/mm3 to 300 mJ/mm3. In some embodiments, the applied electrical energy per volume of volume may be at least 10 mJ/mm3.

In some embodiments, the electrical field produced by each pulse may be at least 1 kV/cm at the peak amplitude of the pulse. The electrical field produced by each pulse may also be at least 10 kV/cm at the peak amplitude of the pulse. The electrical field produced by each pulse may be in the range of 1 kV/cm to 300 kV/cm at the peak amplitude of the pulse. The electrical field produced by each pulse may be in the range of 10 kV/cm to 100 kV/cm at the peak amplitude of the pulse.

In some embodiments, the number of electrical pulses during a single treatment may be at least 10. The number of pulses may also be at least 100. Yet, the number of pulses may be at least 1,000. The number of pulses may be less than 10,000.

In one embodiment, this treatment may be an in vivo treatment of tissue (e.g., including tumors and abnormal growths) of a human subject comprising at least one treatment session, i.e. administration of the electrical energy to the tissue. This treatment may comprise applying electrical energy to the tissue comprising delivering at least one electrical pulse with a pulse duration in the range of 0.01 ns to 1,000 ns, and forming an electrical field in the tissue. This pulse duration may also be in the range of 1 ns to 100 ns, or in the range of 1 ns to 30 ns.

In some embodiments, the electrical field formed by each pulse at the peak amplitude of the pulse may be at least 1 kV/cm; at least 10 kV/cm; in the range of 1 kV/cm to 1,000 kV/cm. Applying electrical energy may comprise applying at least 10 pulses during a treatment, at least 100 pulses, or at least 1,000 pulses. The applied electrical energy per volume of tissue may be at least 10 mJ/mm3, at least 100 mJ/mm3, at least 1,000 mJ/mm3, or in the range of 10 mJ/mm3 to 10,000 mJ/mm3.

The sub-microsecond pulsed electric fields can have pulse lengths of between 0.1 and 1000 nanoseconds. The sub-microsecond pulsed electric fields can have pulse lengths of between 10 and 900 nanoseconds. The sub-microsecond pulsed electric fields can have pulse lengths of about 100 nanoseconds. The sub-microsecond pulsed electric fields can have pulse amplitudes of at least 20 kilovolts per centimeter.

Figure 6:
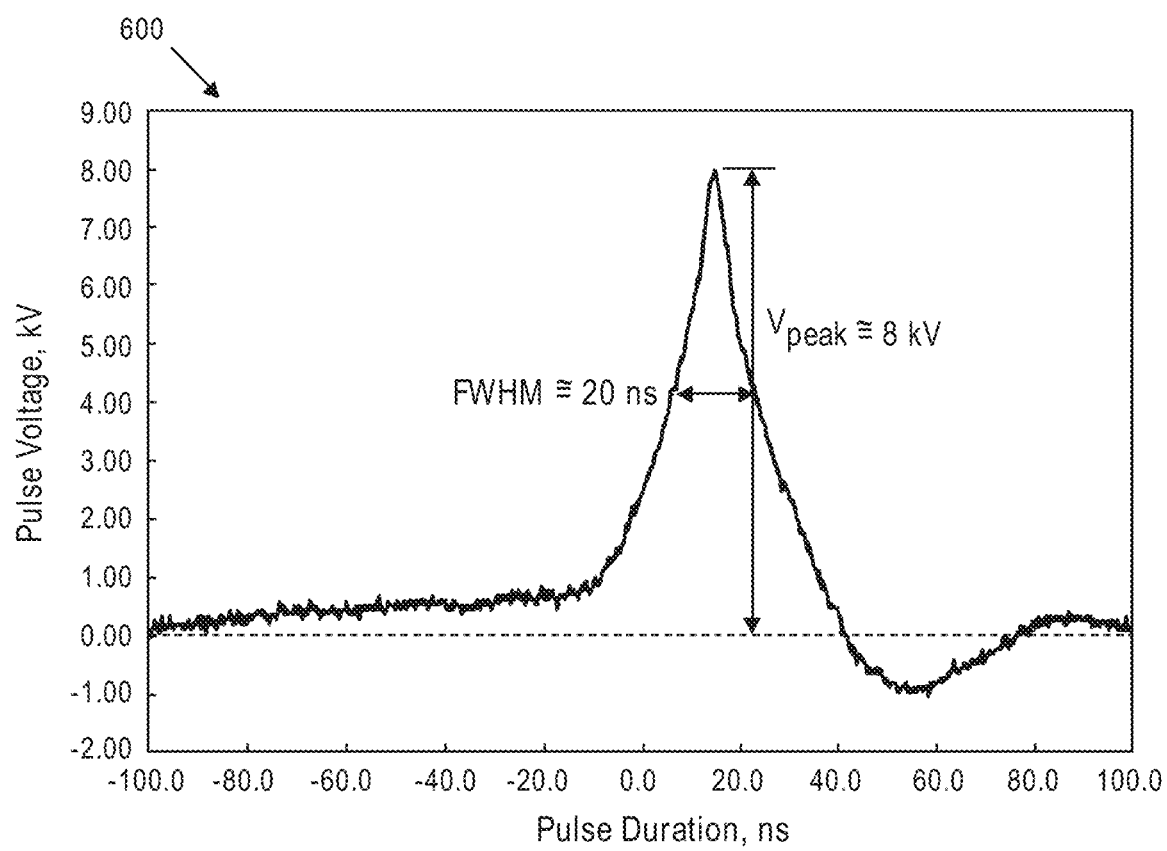
FIG. 6 illustrates an example profile of an electrical pulse, in accordance with embodiments of the present disclosure.

FIG. 6 illustrates an example profile 600 of an electrical pulse, in accordance with embodiments of the present disclosure.

In some embodiments, the electrical pulse may have a duration varying in the range of about 7 nanoseconds (ns) at FWHM to about 20 ns at FWHM. As shown in the figure, the electrical pulse may have a duration of about 20 ns at FWHM and a peak amplitude of about 8.00 kV.

Figure 7:
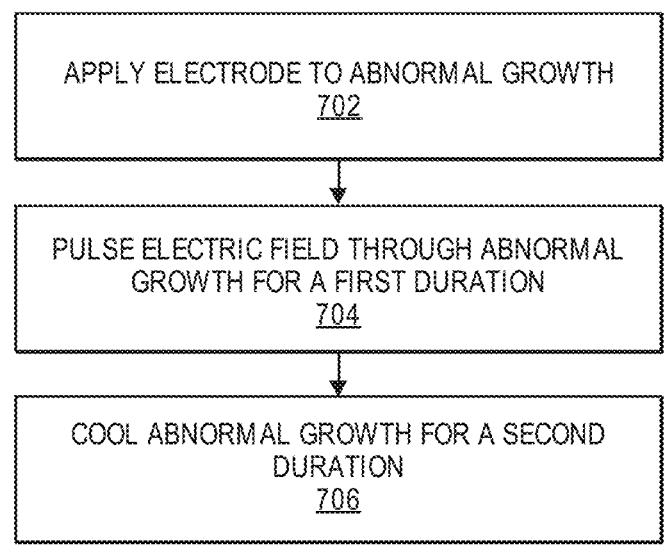
FIG. 7 illustrates a flow chart depicting a method of utilizing pulsing with cooling, in accordance with embodiments of the present disclosure.

FIG. 7 illustrates a flow chart depicting a general method of utilizing electroporation with cooling. It should be noted that the steps shown in this figure may be performed in various orders and some steps may be performed concurrently.

At step 702, an electrode can be applied to an abnormal growth of a subject. This electrode can be electrically coupled to a generator, such as the generator shown in FIG. 2, which is configured to produce sub-microsecond electric pulses. The electrode may conduct these sub-microsecond electric pulses and carry them to the abnormal growth. It should be noted that, in some embodiments, an electrode is not needed at all and sub-microsecond electric pulses may be applied to the abnormal growth or other tissue of the subject without the use of electrodes. In such embodiments, step 702 may not need to be performed.

At step 704, an electric field is pulsed through the abnormal growth for a first duration using the sub-microsecond electric pulses conducted by the electrode. In some embodiments, the first duration may range from the duration of a single pulse to 30 minutes.

In some embodiments, the electric field has an intensity of more than 1 kV/cm. In some embodiments, a width of each of the sub-microsecond electric pulses is between 1 ns and 1000 ns. The intensity of the electric field may be sufficient to trigger apoptosis of the cells in the abnormal growth without a temperature change. The electric field introduced to the abnormal growth at this step may open pores in the cell membranes of the cells in the abnormal growth. In this respect, this electric field may be different from the electromagnetic radatiation used in other ablation modalities (e.g., RF ablation), which is used to heat up or burn the cells of the abnormal growth.

In some embodiments, the intensity of the electric field may be between 0.5-70 kV/cm, or it may be between 5 to 7 kV/cm, or it may be between 1.8-7 kV/cm. In some embodiments, the sub-microsecond electric pulses produced by the generator may be pulsed at a frequency of 100 Hz. In some embodiments, the sub-microsecond electric pulses produced by the generator may be pulsed at a frequency of about 50-500 Hz. In some embodiments, the sub-microsecond electric pulses produced by the generator may be pulsed at a frequency of up to 1000 Hz. In some embodiments, the number of total pulses may range from 50-700 pulses. In some embodiments, the width of each pulse may be 300 ns, or it may be 100 ns.

At step 706, the abnormal growth is cooled for a second duration. This cooling may be performed in various ways. For instance, an ice pack or cooling pack may be applied to the abnormal growth, or the cooling may be performed via perfusion by injecting saline into the subject (e.g., at or around the abnormal growth). Any suitable method for reducing the temperature of the abnormal growth may be used.

In some embodiments, this cooling may lower the temperature of the abnormal growth to be between zero degrees Celsius and twenty degrees Celsius, thereby inhibiting resealing of pores opened by the electric pulses (e.g., at step 704). In some embodiments, the cooling may lower the temperature of the abnormal growth to approximately two degrees Celsius. For example, applying ice (which is at zero degrees Celsius) to the abnormal growth may lower the temperature of the abnormal growth to be close to zero degrees Celsius. However, due to the ambient temperature of the surroundings (e.g., room temperature), the temperature of the abnormal growth may be lowered to just above zero (e.g., approximately two degrees Celsius).

In some embodiments, the second duration for the cooling may be at least five minutes. In some embodiments, the second duration may be under one hour. In some embodiments, the second duration is approximately between fifteen and thirty minutes. In some embodiments, cooling the abnormal growth for the second duration may occur immediately following the first duration. Thus, the electric field is applied through the abnormal growth for the first duration and then, immediately after, the electric field is removed and the abnormal growth is cooled for the second duration.

However, in some embodiments, cooling the abnormal growth for the second duration may occur at least in part during the first duration. Thus, the cooling may be concurrent with the application of the electric field or at least a portion of the cooling may overlap with the application of the electric field (e.g., the second duration may overlap the first duration).

The combination of step 704 and 706 (pulsing the electric field and cooling the abnormal growth) may cause a synergistic stimulation of apoptosis. The underlying mechanism may involve the electric field opening pores in the cellular membranes of the cells of the abnormal growth. The term cellular membranes may include plasma membranes and/or the membranes of intracellular organelles. The cells may have self-repair and homeostatis mechanisms for resealing those pores, but the application of cooling may inhibit or slow the rate at which the cells can reseal the open pores (and thus, prolonging a state of permeabilization of the cellular membranes). The combination may result in at least a 25% reduction in ablated tissue cell survival as compared to the cell survival rate of ablated tissue subjected to pulsing alone without cooling. Alternatively, the reduction may be between 25% to 80%, between 70-80%, between 40-75%, and approximately 60%. In some embodiments, this reduction may be measured at 0.5 hr after cooling, 1.5 hr after cooling, at 3 hr after cooling, at 5 hr after cooling, or at 23 hr after cooling. In some embodiments, this reduction may be measured at 1.5-3 hr after cooling, or it may be measured at 5-23 hr after cooling. In some embodiments, the combination of pulsing the electric field may result in 75% lethality of cells in the abnormal growth when measured at 0.5 hr after cooling.

A major obstacle to wider use of nsEP is the limited output voltage of existing pulse generators. This requires certain compromises to be made in order to achieve the desired ablation efficiency. For example, in order to produce electric pulses of sufficient intensity and voltage, pulse generators may be large and bulky and draw a great deal of power. The limits on output voltage may also limit the size of the ablation zone, which requires multiple electrode insertions and exposures when treating bigger tumors. Thus, increasing the ablation efficiency by combining pulsing the electric field with cooling according to the present disclosure may allow existing pulse generators to be used without current limits on the size of the ablation zone. In some cases, the increased ablation efficiency may serve to minimize the side effects of ablation.

Alternatively, the increased ablation efficiency provides benefits of using a lower number of pulses or lower pulse strength (since a lower number of pulses or lower pulse voltage will be needed to achieve the same cell mortality), which also enables pulse generators to be designed to be smaller and operate on less power while still providing effective ablation. Accordingly, the synergy of the pulsing and cooling steps may provide substantially the same ablation efficiency (as that of performing pulsing without any cooling) while allowing one or more of the following: 1) lowering pulse voltage, 2) lowering pulse numbers, or 3) increasing a distance between electrodes. As an example, the increased ablation efficiency may allow a 2-5 fold reduction in the pulse intensity to achieve the same results (e.g., measured by degree of cell mortality, survival rate, and so forth) as an application of nsEP without any cooling. For instance, nsEP applied without cooling may require a pulse intensity of 10-30 kV/cm to achieve the same results as applying nsEP with a pulse intensity of 1-7 kV/cm in combination with cooling.

In some embodiments, the nsEP may have an intensity that is sufficient to trigger apoptosis on its own (e.g., without cooling), but the use of cooling with the nsEP may improve the ablation efficiency and increase the degree of cell mortality. However, in other embodiments, the nsEP may have an intensity that is too low to trigger apoptosis on its own without cooling. However, the combined use of the nsEP and cooling may result in apoptosis despite either step being unable to trigger apoptosis on their own.

Disclosed now are supporting results of two studies revealing the synergistic effects of combining nanosecond electric pulses and cooling, in regards to the improved ablation efficiency associated with inducing apoptosis in cancerous tumors and abnormal growths on/in a subject. The first study entitled "*The cytotoxic synergy of nanosecond electric pulses and low temperature leads to apoptosis*" is discussed in reference to FIGS. 8-11. The second study entitled, "*Effect of cooling on cell volume and viability after nanoelectroporation*" is discussed in reference to FIGS. 12-16.

Study 1: Abstract

The results of Study I show the efficient induction of apoptosis even by a non-toxic nsEP exposure when it is followed by a 30-min chilling on ice. This chilling itself had no impact on the survival of U-937 or HPAF-II cells, but caused more than 75% lethality in nsEP-treated cells (300 ns, 1.8-7 kV/cm, 50-700 pulses). The cell death was largely delayed by 5-23 hr and was accompanied by a 5-fold activation of caspase 3/7 (compared to nsEP without chilling) and more than 60% cleavage of poly-ADP ribose polymerase (compared to less than 5% in controls or after nsEP or chilling applied separately). When nsEP caused a transient permeabilization of 83% of cells to propidium iodide, cells placed at 37° C. resealed in 10 min, whereas 60% of cells placed on ice remained propidium-permeable even in 30 min. The delayed membrane resealing caused cell swelling, which could be blocked by an isosmotic addition of a pore-impermeable solute (sucrose). However, the block of swelling did not prevent the delayed cell death by apoptosis. The potent enhancement of nsEP cytotoxicity by subsequent non-damaging chilling may be a powerful tool, for example, in tumor ablation therapies.

Study I shows that the cytotoxicity of nsEP can be greatly increased by a brief cooling after exposure to electric pulses. When neither nsEP alone nor cooling alone affected cell survival, their combination triggered apoptosis and culminated in 75% cell loss at 23 hr. The likely cause of this strong synergy was hampered resealing of electroporated cells at lower temperatures, which aggravated the disruption of cell homeostasis. However, the facilitation of the colloid-osmotic swelling played little or no role in the induction of the delayed cell death.

Study 1: Materials and Methods

Cell Lines and Media

In Study I, U-937 (human monocyte lymphoma) cells were used. This cell line was chosen because the response of U-937 to electric pulses has been extensively investigated in the field. U-937 and HPAF-II (human pancreatic adenocarcinoma) cells were obtained from ATCC (Manassas, Va.). U-937 grow in suspension and were cultured in RPMI-1640 medium (Sigma-Aldrich, St. Louis, Mo.). HPAF-II grow in a monolayer and were kept in EMEM medium (ATCC). Both growth media were supplemented with L-glutamine (ATCC), 10% (v/v) fetal bovine serum (Atlanta Biologicals, Norcross, Ga.), 100 U/ml penicillin and 0.1 mg/ml streptomycin (Mediatech Cellgro, Herdon, Va.).

nsEP Exposure Methods

Cell samples were exposed to nsEP in 1 mm gap electroporation cuvettes (BioSmith, San Diego, Calif.) at room temperature.

U-937 cells were resuspended at 1.2 to $5 \times 10^6$ cell/ml in fresh RPMI medium. For certain experiments, the medium was supplemented with 25 mM HEPES to maintain the pH 7.4 while outside the incubator. 100-μl samples were loaded in the electroporation cuvettes and subjected to either nsEP or sham exposure.

Trapezoidal pulses of 300 ns duration and 700 V amplitude from an AVTECH AVOZ-D 2-B-ODA generator (AVTECH Electrosystems, Ottawa, Ontario, Canada) were delivered to electroporation cuvettes via a 50- to 10-Ohm transition module (AVOZ-D2-T, AVTECH Electrosystems) modified into a cuvette holder. Pulse trains of predetermined duration, at the selected repetition rate of 100 Hz, were triggered externally from a model S8800 stimulator (Grass Instrument Co., Quincy, Mass.). The pulse amplitude and shape were monitored using a 500 MHz, 5 GS/s TDS 3052B oscilloscope (Tektronix, Wilsonville, Oreg., USA).

nsEP exposure of HPAF-II cells without detachment from the substrate was accomplished by growing the cells on glass coverslips with an indium tin oxide (ITO) conductive layer, and loading these coverslips in RPMI-filled electroporation cuvettes. The ITO layer was deposited on one side of glass coverslips (#0 thickness, 8 mm diameter) by Diamond Coatings (Halesowen, UK). For better cell adherence, the ITO surface was treated with poly-1-lysine. Cells were seeded at $3 \times 10^4$ cells per coverslip and cultured overnight in the growth medium. Cells were exposed to 700 pulses (300 ns, 100 Hz) at 600 V, which generated practically uniform electric field of 1.8 kV/cm at the coverslips surface.

Post-nsEP Treatment Protocols

Immediately following nsEP exposure, cuvettes were placed on ice or in a water bath at 37° C. for 30 min. The temperature of the samples in the different settings was measured using a thermocouple thermometer (Pysitemp, Clifton, N.J.). The temperature of the samples by the end of 30-min incubation on ice and in the water bath averaged 1.6 and 36.1° C., respectively.

To block cell swelling, sucrose was used. Sucrose is a nanopore-impermeable sugar, which was shown to prevent the osmotic water uptake caused by nsEP. U-937 cells ($5 \times 10^5$/sample) were exposed to nsEP in complete RPMI medium plus 25 mM HEPES and immediately afterward mixed 7:3 with an isosmotic water solution of sucrose (290 mOsm/kg, 280 mM) to yield the fractional osmolality due to sucrose of 87 mOsm/kg. Samples were moved to the different temperatures for 30 min and then diluted 5× with fresh medium. Parallel controls were diluted the same way, but with an isosmotic meso-erythritol solution instead of sucrose. Meso-erythritol is a small sugar, which does not prevent water uptake and therefore served as a control for the equivalent dilution of the medium.

Propidium Iodide Permeability Assay

Permeability to propidium iodide (PI) was used to measure the kinetics of plasma membrane resealing after nanoelectroporation. Immediately after nsEP exposure all samples were diluted 1:1 with RPMI and placed at 37° C. in the water bath or on ice. At 0, 10, or 30 min post exposure, 20 μl of each cell sample was mixed with an equal volume of 50 μg/ml PI (Sigma) in PBS and placed at 37° C. for 5 min. Cell samples were loaded into a counting chamber of Cellometer Vision (Nexcelom Bioscience LLC, Lawrence, Mass.) and both bright field transillumination and fluorescence images were acquired. The cell diameters and PI fluorescence intensity of 300-500 cells per sample were measured from the image and logged using Cellometer software. Images were generated using Grapher 11 (Golden Software, Golden, Colo.).

Viability Assays

After exposure to nsEP, cell survival was measured either every hour for 23 hr, using the luminescence-based metabolic cell viability assay Real Time-Glo MT (Promega Corporation, Madison, Wis.), or at 23 hr, using a resazurin-based metabolic assay Presto Blue (Life Technologies, Grand Island, N.Y.).

To monitor cell survival over 23 hr, U-937 cells were exposed to nsEP in complete RPMI medium with 25 mM HEPES and then incubated on ice or in the water bath at 37° C. for 30 min. Next, the cells were seeded in triplicates in white-wall 96-well plates, the Real Time-Glo reagent was added, and samples were kept in the incubator with 5% $CO_2$ for 1 hr. Plates were then sealed from the sides with parafilm and luminescence was acquired every hour using a Synergy 2 microplate reader set at 37° C. (BioTek, Winooski, Vt.). The triplicate data were averaged, corrected for the background, and considered as a single experiment.

For the Presto blue assay, immediately following the incubation on ice or at 37° C. in the water bath, the cell samples were moved to a 96-well plate (for U-937 cells) or to a 48-well plate (for the HPAF-II on the ITO-coverslips) and incubated for 22 hr before the addition of the Presto Blue reagent for 1 hr. The plate was read with the Synergy 2 microplate reader, with excitation/emission settings at 530/590 nm.

Caspase 3/7 Activity

Caspase activation was measured at 4.5 hr after nsEP using Caspase-Glo 3/7 assay from Promega Corporation, concurrently with measuring cell viability in the same samples. We first recorded fluorescence (Presto Blue/viability) and then added the Caspase-Glo 3/7 assay according to manufacturer's instructions. Briefly, after the post-nsEP treatments, U-937 cells were plated and incubated at 37° C. in 5% $CO_2$ humidified air. The Presto Blue reagent was added 1 hr before measurement. Finally, cell samples were lysed with the Caspase-Glo 3/7 reagent and incubated at room temperature for 1 hr before recording the luminescence signal. As a positive control for apoptosis induction, U-937 were treated with 10 μm staurosporine for 4.5 hr. All conditions were done in triplicates, the data were averaged, corrected for the background, and considered as a single experiment.

Western Blot and Quantification of Poly-ADP Ribosome Polymerase (PARP) Cleavage

Cleavage of PARP-1 in fragments of 89 and 24 kDa is an established hallmark of apoptosis. This cleavage is executed by caspases 3 and 7, proteases activated during apoptosis. Both the full-length 116 kDa PARP and its 89 kDa fragment can be detected together by immunoblotting allowing for the quantitation of the apoptotic fraction of cells from the relative amounts of intact and cleaved PARP.

At 4.5 hr after nsEP treatment, $5 \times 10^5$ cells per sample were lysed in a buffer containing 20 mM HEPES (pH 7.5), 200 mM NaCl, 10 mM EDTA, 1% Triton X-100, supplemented with the SIGMAFAST cocktail of protease inhibitors (Sigma). Proteins in the lysate were separated by electrophoresis on a NuPAGE 4-12% Bis-Tris SDS-polyacrylamide gel (Life Technologies) and then transferred to Immune-Blot Low Fluorescence PVDF membrane (Bio-Rad Laboratories, Hercules, Calif.). The membranes were blocked in the Odyssey blocking buffer for 1 hr at room temperature (LI-COR Biosciences, Lincoln, Nebr.). The primary rabbit anti-PARP polyclonal antibody (Roche Diagnostics GmbH, Mannheim, Germany) was diluted 1:2,000 in the Odyssey blocker with 0.2% Tween-20. The secondary donkey anti-rabbit IgG (H+L) antibody, conjugated with an infra-red fluorophore IRDye-680LT (LI-COR Biosciences), was diluted 1:20,000 in the same buffer. The membranes were incubated at room temperature with primary and secondary antibodies for 2 hr and 1 hr, respectively.

The membranes were imaged using Odyssey 9120 Infra-red Imaging System (LI-COR Biosciences) in the 700 nm channel. The images were quantified using MetaMorph software (Molecular Devices, Foster City, Calif.).

The fraction of the cleaved PARP (K, %) was calculated as: $K=100\times 1.3S/(1.3S+L)$ where L and S are the fluorescence intensities of the 116 kDa full-length PARP and of the 89 kDa PARP fragment, respectively. The coefficient 1.3 was used for S mass correction. As a positive control, apoptosis was induced using 10 µM staurosporine for 4 and 6 hr.

Statistical Analysis

Data are presented as mean+/−SE for n independent experiments. Statistical analyses were performed using a two-tailed t-test where $p<0.05$ was considered statistically significant. Statistical calculations, including data fits, and data plotting were accomplished using Grapher 11 (Golden Software).

Study 1: Results

Post-nsEP Cooling Induces Cell Death

Figure 8A:
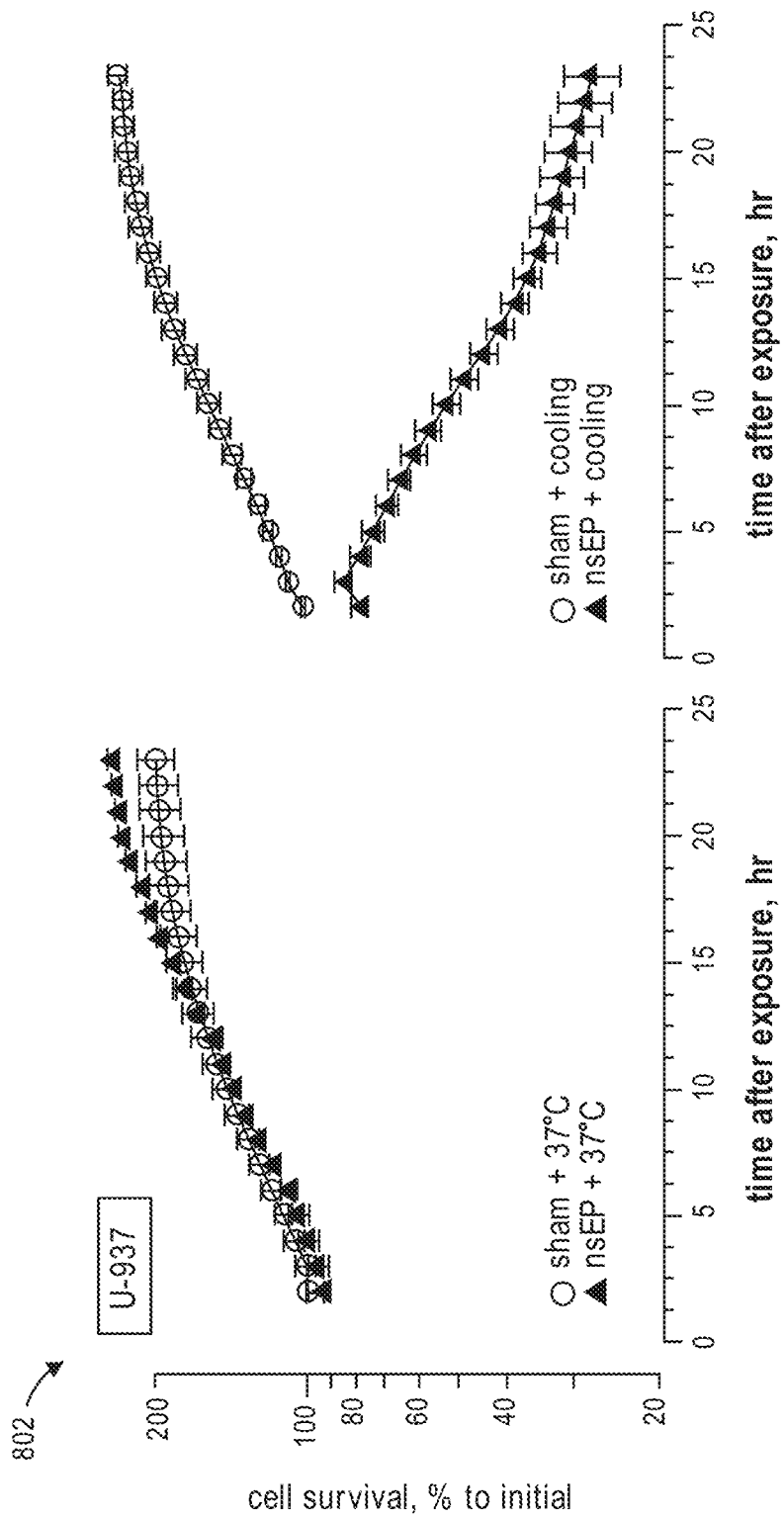
FIGS. 8A-8B illustrate graphs depicting the effect of cooling after nanoelectroporation on survival of different cell types, in accordance with embodiments of the present disclosure.
Figure 8B:
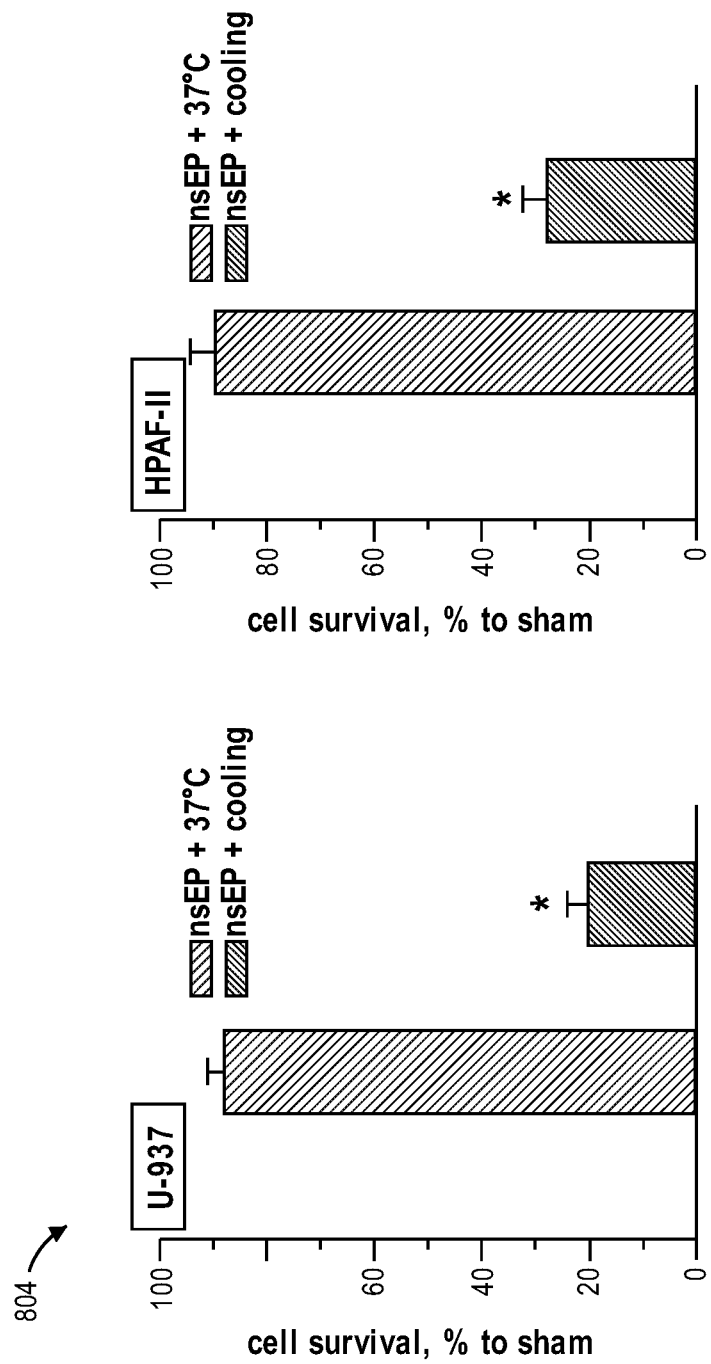

To study the effect of temperature on cell survival after EP exposure, U-937 cells were exposed at room temperature (RT) to 50, 300-ns, 7 kV/cm pulses delivered at 100 Hz. FIGS. 8A-8B illustrate the effect of cooling after nanoelectroporation on survival of different cell types. Immediately after the exposure, samples were either placed on ice, or moved into a 37° C. water bath. Parallel sham-exposed samples were incubated at the different temperatures the same way. In 30 min, all cell samples were plated and cell survival was measured every hour (from 2 to 23 hr post exposure) using the luminescence-based metabolic viability assay Real Time-Glo MT (FIG. 8A). Already at 2 hr post exposure the survival of pulsed cells exposed to transient cooling was diminished. It kept declining over time to about 25% of the starting level, whereas the same nsEP treatment alone or the same cooling alone caused no cell death and did not decelerate cell growth. Graphs 802 of FIG. 8A show changes of cell survival in U-937 cells subjected to either sham or nsEP exposure (50 pulses, 300 ns, 7 kV/cm, 100 Hz) followed by a 30-min incubation either at 37° C. or on ice. The survival was monitored from 2 to 23 hr using a Real Time-Glo metabolic assay; the luminescence in "sham+37° C." group at the earliest timepoint (2 hr) was taken as 100%. Mean+/−s.e for n=3-6.

The synergistic effect between nsEP and cooling was confirmed when using a different cell line, different pulse parameters, a different exposure procedure, and survival assay (FIG. 8B). Graph 804 of FIG. 8B shows that cell survival is profoundly reduced by nsEP+cooling, but not by nsEP alone. Cell survival was measured at 23 h post nsEP exposure of U-937 cells in suspension by the Presto blue assay and expressed in % to sham-exposed parallel control at 23 hr. The nsEP exposure was 50 pulses, 300-ns pulses, at 7 kV/cm, 100 Hz for U-937 cells (FIG. 8A) and 700, 300-ns pules at 1.8 kV/cm, 100 Hz for HPAF-II cells on ITO coverslips (FIG. 8B). Mean+/−s.e. for n=6-8, *p<0.001. In both these cell lines, nsEP exposure alone had little if any effect on cell survival, whereas its combination with cooling caused 70-80% cell loss (p<0.001).

Cooling nsEP Treated Cells Blocks Membrane Resealing and Induces Cell Swelling

Figure 9A:
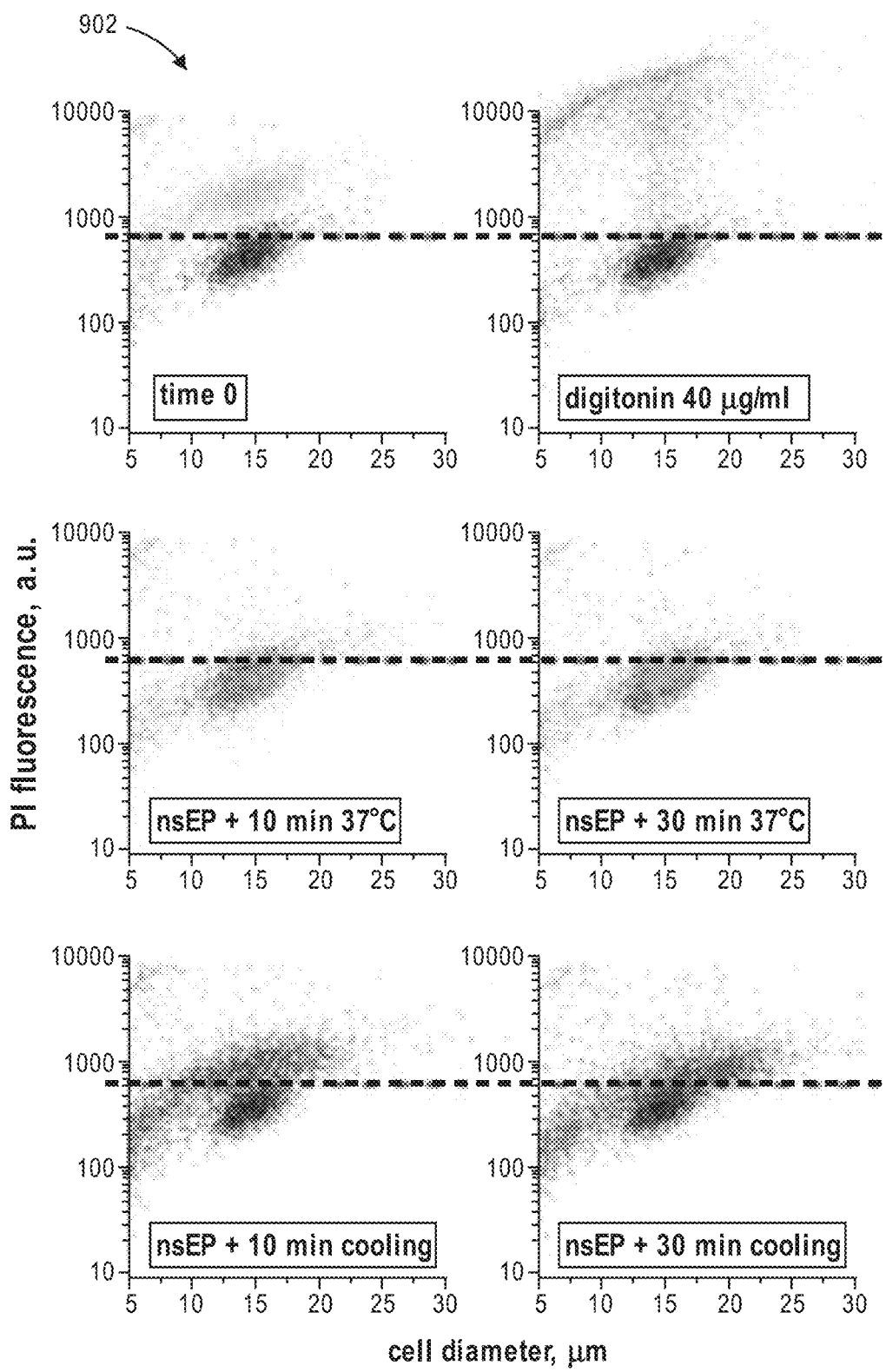
FIGS. 9A-9C illustrate graphs depicting how cooling after nsEP exposure delays membrane resealing, in accordance with embodiments of the present disclosure.
Figure 9B:
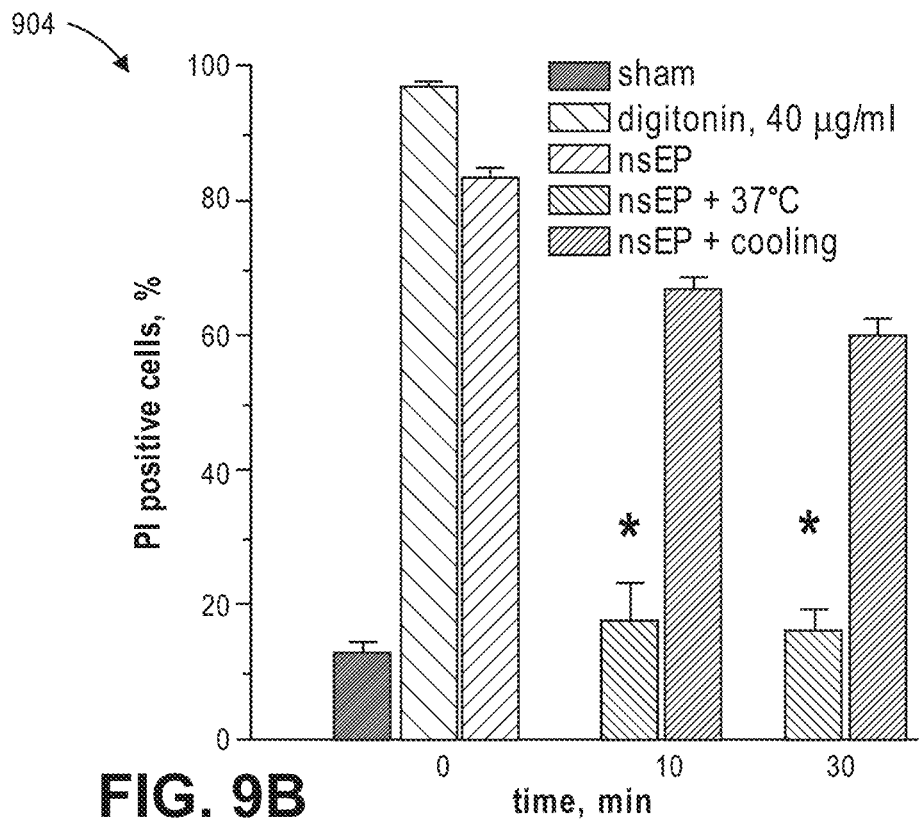
Figure 9C:
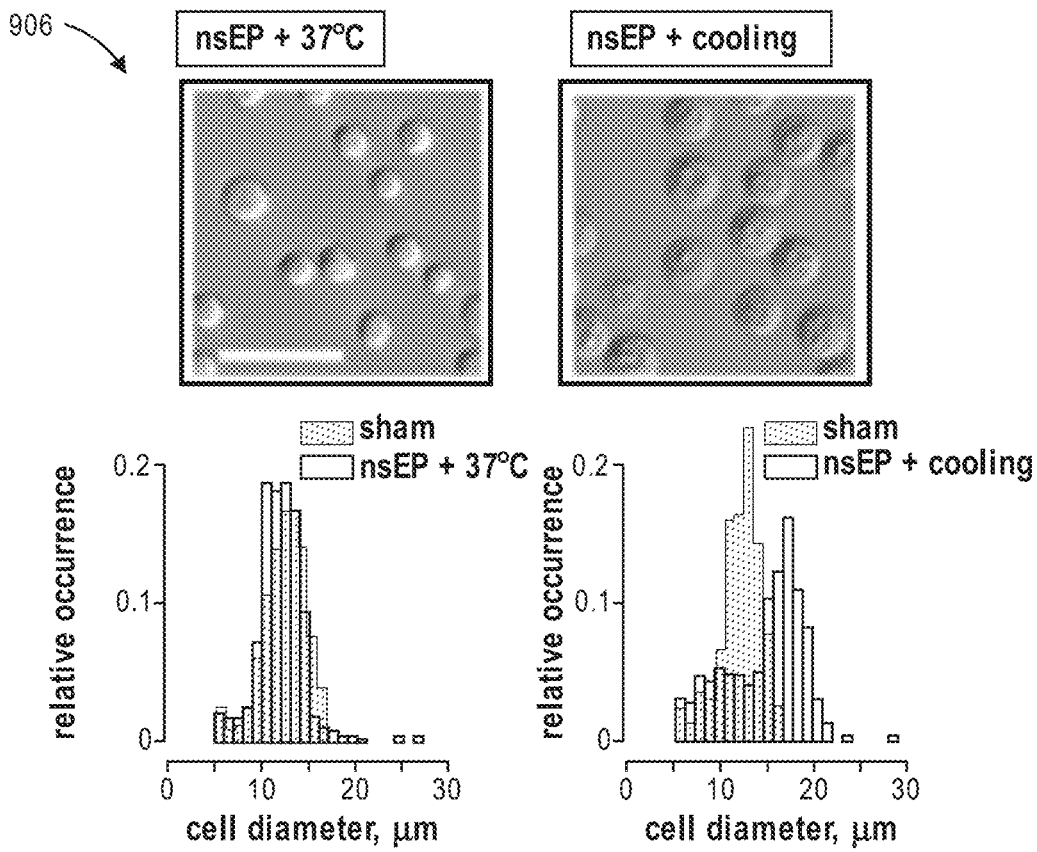

FIGS. 9A-9C illustrate how cooling after nsEP exposure delays membrane resealing, resulting in cell swelling. In order to measure the effect of temperature on membrane resealing, U-937 cells were exposed to 50 pulses, 300 ns, 100 Hz, 7 kV/cm, at room temperature, followed by incubation either on ice or at 37° C. Propidium iodide (PI) was added to the cells either immediately after nsEP ("time 0"), or after 10 or 30 min of incubation at different temperatures. Since PI is permeable for open cell membranes, the uptake of PI by the cells serves as a proxy for measuring membrane resealing. Thus, the time course of membrane resealing after a nsEP insult (50 pulses, 300 ns, 7 kV/cm, 100 Hz) was assessed by propidium iodide (PI) entry and osmotically-driven swelling in U-937 cells.

Graphs 902 of FIG. 9A show the effect of post-nsEP incubation time and temperature on PI uptake and cell diameter in individual cells, by comparing the PI uptake and cell diameters in two nsEP treatments (nsEP followed by room temperature, and nsEP followed by cooling) to a control, in which cells were permeabilized with 40 µg/ml digitonin for 5 min. The dots in the graphs 902 represent individual cells and the horizontal dashed lines in the graphs 902 show the fluorescence threshold to identify PI-positive cells. The fraction of the cells above the horizontal dashed line (e.g., identified as PI-positive cells for having a fluorescence above the fluorescence threshold) in each of the different treatments shown in graphs 902 is plotted in graph 904 of FIG. 9B for clarity.

From graph 904 of FIG. 9B, it can be seen that, immediately after the exposure to nsEP (e.g., time=0), 83+/−1.2% cells were permeable to PI, suggesting that nsEP opens PI-permeable pores in the cell plasma membrane. At 10 min post exposure, cells incubated at 37° C. were already impermeable to PI (suggesting that the membrane reseals rapidly without cooling), whereas 67+/−1.4% of the cells incubated on ice remained permeable to PI (p<0.001). The effect of cooling on membrane permeability became even more prominent at 30 min, when 60+/−5.5% of the cells remained permeable to PI (FIGS. 9A-9C). Mean+/−s.e. for n=3, *p<0.001 for the effect of cooling vs 37° C.

This increase in membrane permeability associated with nsEP+cooling corresponds to an increase in PI uptake that results in osmotically-driven swelling in the U-937 cells. This swelling in the cells and the accompanying increase in cell diameter can serve as a visual indicator of increased membrane permeability. For instance, the graphs 906 of FIG. 9C provide a visual comparison of cells exposed to nsEP+cooling compared to cells exposed to just nsEP. Scale bar: 50 µm. In particular, the right image shows cells exposed to nsEP+cooling for 30 minutes, which display profound swelling and a drastic morphologic change resembling what is observed in cells after a hypotonic stress. The reason for the post-nsEP swelling in the isosmotic medium is the presence of the large intracellular solutes, which remain membrane impermeable after nsEP, thereby creating a colloid-osmotic gradient to attract water. The graphs 906 of FIG. 9C also show histograms providing a comparison of diameters between cells exposed to nsEP+cooling and cells exposed to just nsEP. The histogram data are 300-500 cells measured per sample from 3 independent experiments, and the filled bars in the histograms show the distribution of cell diameters in sham-exposed control samples. As can be seen from FIG. 9C, the modal diameter of nsEP-treated cells incubated on ice increased to 16.5 μm compared to 12.8 μm in cells incubated at 37° C. following exposure to nsEP. Cells exposed to nsEP followed by incubation at 37° C. were not different in appearance or size from the controls (e.g., cells permeabilized with 40 μg/ml digitonin for 5 min).

Sucrose Inhibits Swelling but Fails to Prevent Cell Death Caused by Cooling after nsEP Several studies reported necrosis due to the colloid-osmotic cell swelling as a predominant mechanism of cell death after exposure to nsEP. This mechanism could be blocked by isosmotic addition of a nanopore-impermeable solute (such as sucrose) to the growth medium. The same approach was performed to test if the uncontrolled swelling is responsible for death of cells subjected to cooling after nsEP (rather than the apoptosis triggered by cooling and nsEP). These results are reflected in FIGS. 10A-10B, which illustrate how sucrose inhibits cell swelling but does not prevent cell death caused by combining nsEP with cooling.

Immediately after nsEP exposure (50 pulses, 300 ns, 7 kV/cm, 100 Hz), U-937 cell samples were mixed with a sucrose or meso-erythritol solution to yield the fractional osmolality due to the sugars of 87 mOsm/kg. In contrast to sucrose, smaller meso-erythritol is a porepermeable solute, which is not expected to prevent swelling; therefore it served as a control for possible effect of the dilution of the growth medium. The samples were kept at 37° C. or on ice for 30 min, then aliquots were collected to assess cell diameters. The remaining volumes were diluted 5× with RPMI medium and cell survival was monitored continuously for 23 hr. Sham-exposed control samples were subjected to the same temperature incubation and media dilutions.

Figure 10A:
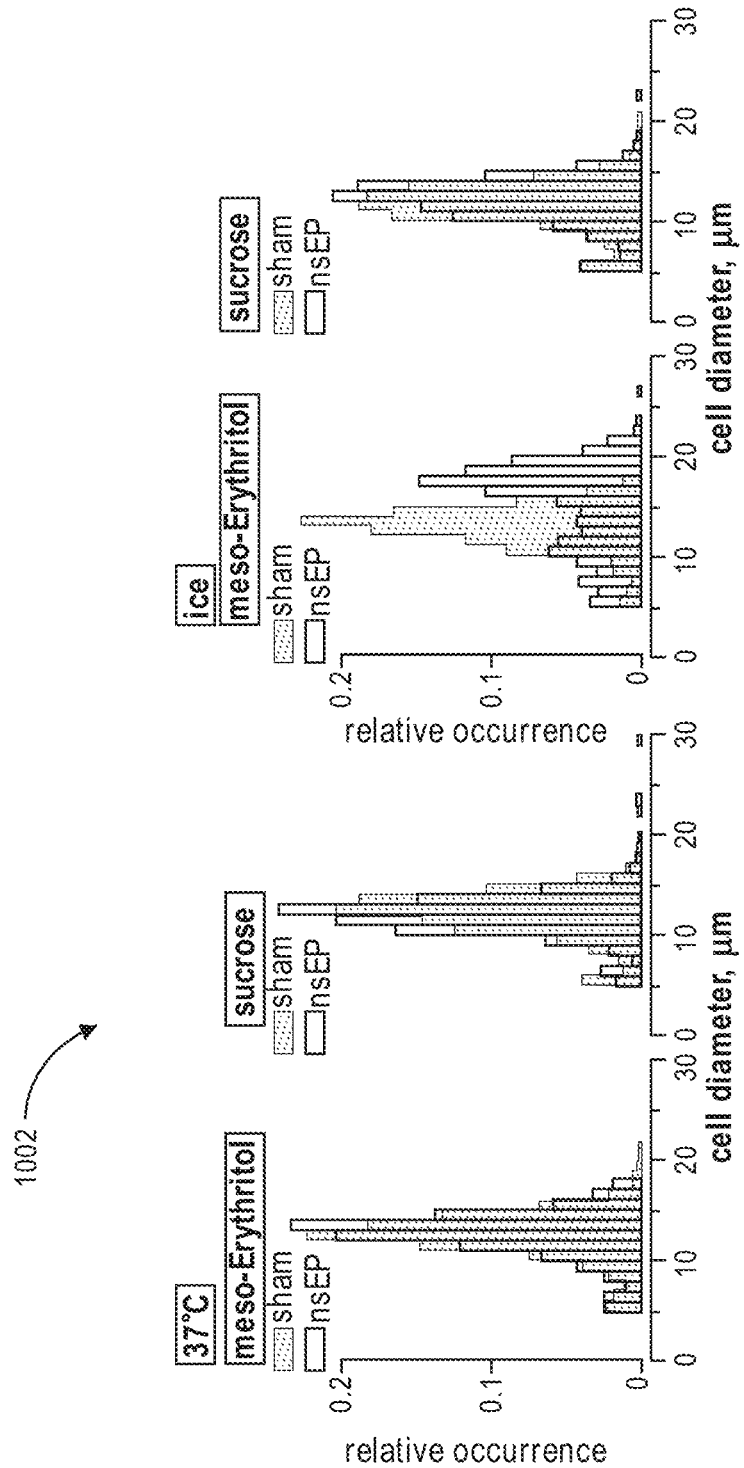
FIGS. 10A-10B illustrate graphs depicting how sucrose inhibits cell swelling but does not prevent cell death caused by combining nsEP with cooling, in accordance with embodiments of the present disclosure.

Graphs 1002 of FIG. 10A illustrate the effect of the two sugars (sucrose or meso-erythritol) on cell diameter in the cases of nsEP followed by incubation at room temperature (nsEP+37° C.) and nsEP followed by cooling (nsEP+ice). The left graph of graphs 1002 corresponds to nsEP+37° C.), and it can be seen that there is no difference in cell diameters between the use of meso-erythritol and sucrose. However, the right graph of graphs 1002 corresponds to (nsEP+ice) and there is a noticeable difference in the cells diameters between the use of the two sugars, which suggests that the use of sucrose in the case of nsEP+ice completely prevented cell swelling.

Figure 10B:
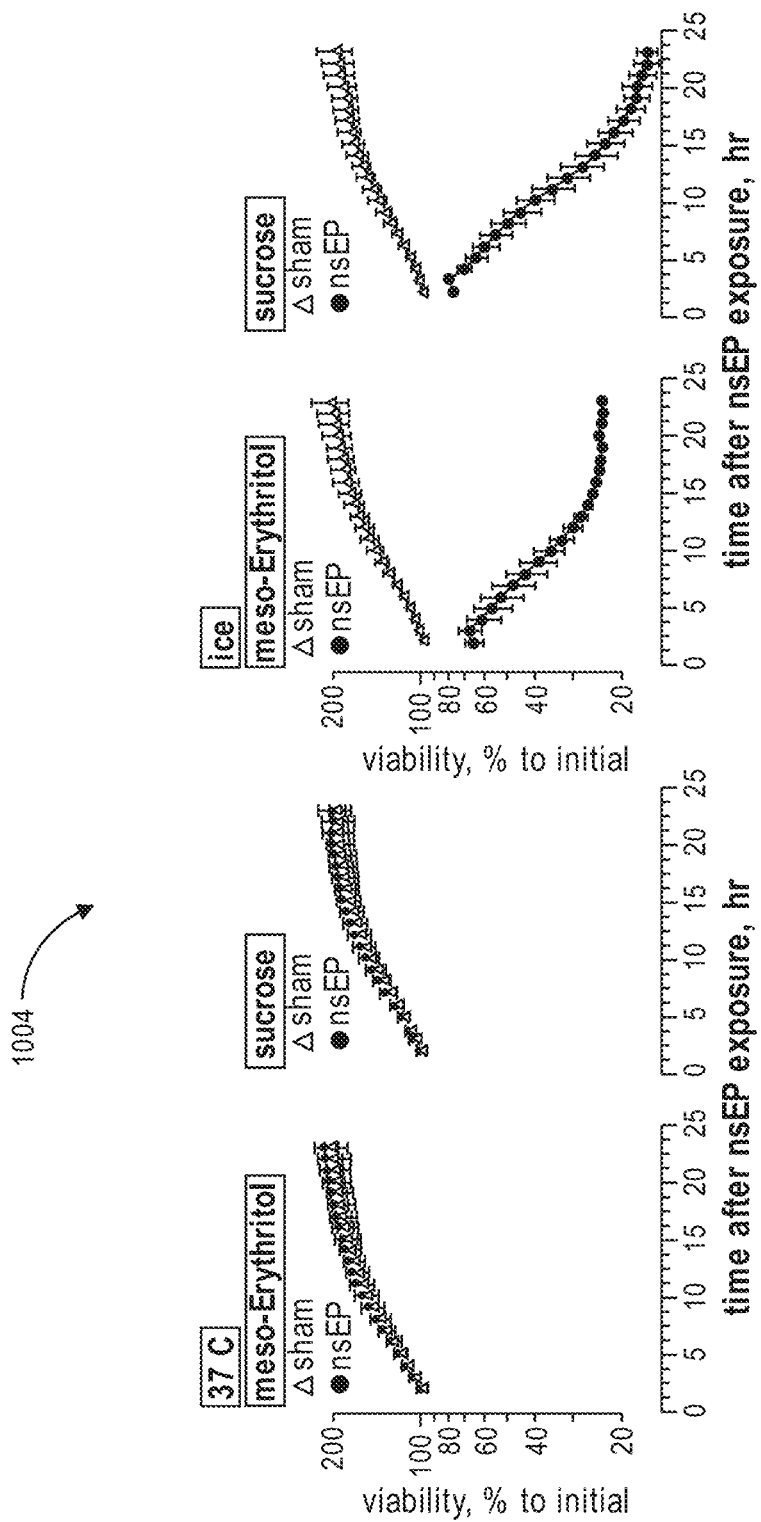

However, graphs 1004 of FIG. 10B illustrate that the use of sucrose, despite preventing cell swelling, does not prevent delayed cell loss caused by the combination of nsEP and cooling. In particular, graphs 1004 of FIG. 10B shows the effect of the two sugars on cell survival during a 23 hr period following nsEP+37° C. (left graph) or nsEP+ice (right graph). In the right graph of graphs 1004, it can be seen that while the use of sucrose over meso-Erythritol improved early cell survival (between 2 and 5 hr following cooling), it did not prevent the delayed cell loss seen when combining nsEP with cooling. At 23 hr, after exposure to nsEP and cooling, the cell survival was similar in the presence or absence of sucrose. The data were normalized to the luminescence value in "sham+37° C." group at the earliest time point (2 hr). Mean+/−s.e. n=3.

Thus, to summarize, FIGS. 10A and 10B show the presence of sucrose prevented the osmotic water uptake, cell swelling and early cell death from the membrane rupture after nsEP exposure followed by cooling, but the rescued cells died later on nonetheless.

Cooling after nsEP Exposure Induces Apoptotic Cell Death

The prevalence of the cell death delayed by as much as 5-15 hr after nsEP, as well as the lack of protection when cell swelling and membrane rupture were inhibited, suggested nsEP followed by cooling could have triggered apoptosis. One way to confirm this is to measure caspase 3/7 activation and PARP cleavage (two actions associated with apoptosis) for cells exposed to the combination of nsEP and cooling. In particular, U-937 cells were exposed to 50, 300 ns pulses (100 Hz, 7 kV/cm) and immediately incubated at 37° C., or placed on ice for 30 min and then in the incubator. An increase in caspase 3/7 activation and PARP cleavage specifically for the cells exposed to nsEP and placed on ice would suggest that nsEP followed by cooling is triggering apoptosis.

Indeed, FIGS. 11A-11B document strong activation of caspase 3/7 and PARP cleavage in U-937 cells after nsEP (50 pulses, 300 ns, 100 Hz, 7 kV/cm) when it was followed by a 30 min cooling. Graph 1102 of FIG. 11A shows the activity of caspase 3/7 and cell survival at 4.5 hr, for cells exposed to both nsEP with or without cooling. For a positive control, apoptosis was induced by incubation with 10 μm staurosporine for 4.5 hr. As can be seen, the activity of caspase 3/7 at 4.5 hr after nsEP was increased 5-fold by cooling.

Graph 1104 of FIG. 11B, shows cell survival at 4.5 hr, for cells exposed to both nsEP with or without cooling. It can be seen that cells exposed to nsEP with cooling have a lower survival rate. From FIGS. 11A and 11B, it can be gathered that the added cooling increases the activity of caspase 3/7 5-fold despite the concurrent 25% cell loss, suggesting that caspase activation could be even more pronounced than in staurosporine-treated positive controls).

Figure 11D:
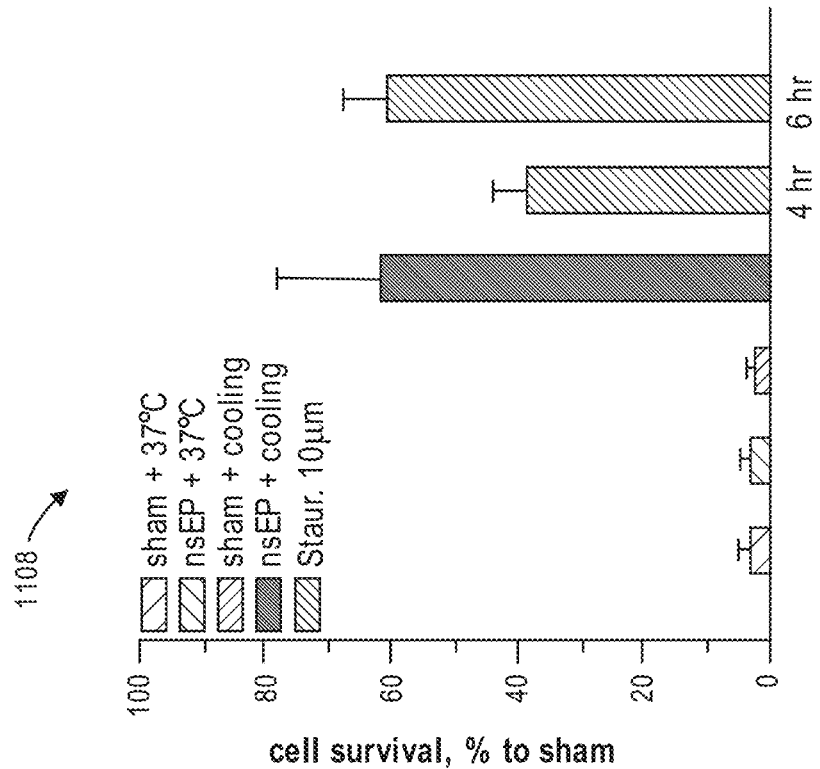
Figure 11C:
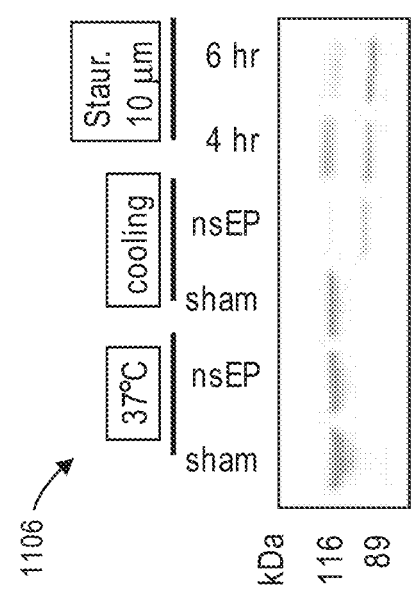

Another employed hallmark of apoptosis, PARP cleavage, is an intrinsically ratiometric assay, which enables to quantify the ratio of apoptotic and non-apoptotic cells. Increased PARP cleavage associated with nsEP and cooling can be seen in graph 1106 of FIG. 11C and graph 1108 of FIG. 11D. Graph 1106 of FIG. 11C shows a representative Western blot for intact and cleaved PARP (116 and 89 kDa, respectively). Graph 1108 of FIG. 11D shows a quantification of the cleaved fraction of PARP. For a positive control, apoptosis was induced with 10 μm staurosporine. Mean+/−s.e. n=6-9 (A, B) or n=3 (C). *p<0.001 for the difference of nsEP+cooling from nsEP+37° C. More than 60% of PARP was cleaved at 4.5 hr after nsEP and cooling; the same nsEP exposure without cooling and the same cooling without preceding nsEP exposure had no effect (<10% of cleaved PARP). Same as with the previous assay (e.g., reflected in FIGS. 11A-11B), the efficiency of nsEP+cooling in inducing apoptosis was comparable or slightly higher than the effect of staurosporine.

Overall, these data demonstrate that cooling after a non-lethal nsEP exposure triggers apoptotic death in most cells.

Study 1: Discussion

This study is the first to show that a brief cooling after nsEP exposure can profoundly increase the cytotoxic effect by the induction of apoptosis. The combined effect is strong even when neither cooling nor nsEP applied separately diminish cell survival, thus highlighting the strong synergistic effect of the two modalities. Cooling may assist nsEP-based ablation therapies by allowing to lower pulse voltage and number, or to increase the distance between electrodes without losing the ablation efficiency. Lowering the voltage may help to minimize side effects such as pain, involuntary muscle contractions, and the risk of arrhythmia when treatments are done in the proximity of the heart.

Cooling nanoporated cells might also help to overcome the diverse cytotoxic efficiency of nsEP among different cell types. A recent study shows that the $LD_{50}$ varied profoundly across several commonly cell types, increasing from 51 J/g for Jurkat to 1861 J/g for HeLa cells. These results suggest that the same ablation protocol may kill one type of cancer but prove very inefficient for another type. This difference might be due to many reasons including plasma membrane physiology or composition, and different abilities to repair nsEP-induced damage.

Restoring the plasma membrane barrier function is mandatory for the cell to survive electroporation. Interestingly, temperature has been shown to affect the cell membrane resealing. Indeed, in this condition nsEP triggered mostly apoptotic cell death.

The data of the present disclosure show that cooling nsEP-treated cells blocks membrane resealing and induces massive cell swelling. This result is consistent with earlier findings using conventional electroporation; for example, Kinosita and Tsong showed that at 3° C. the permeabilized state of electroporated erythrocytes can be maintained for 20 hr. While it was most logical to expect that the loss of cell volume control leads to necrosis (by swelling culminating in membrane rupture), the experiments of the present disclosure showed that it was not the case. In addition to the necrotic cell death seen at about 2 hr post exposure, cooling pulsed cells caused a gradual cell loss that reached maximum at 23 hr after treatment. The long term cell death correlated with a strong activation of caspases and cleavage of PARP denoting the activation of the apoptotic cell death pathway.

The relatively low level of cell death seen at 2 hr after exposure suggests that, once placed in the incubator, cells, which underwent nsEP+cooling treatment, reseal and regain control over their size. A critical question is therefore what triggers apoptosis in these cells. Alterations in the homeostasis of several physiological ions have been shown to influence apoptosis.

As nsEP affect also intracellular membranes, cooling may increase cell death by prolonging the permeabilized state of intracellular organelles. NsEP have recently been shown to permeabilize nuclear envelope and mithocondria membrane. Mithocondria play a crucial role in apoptotic cell death. The disruption of the mithocondria barrier function causes the release of apoptosis-inducing proteins such as cytochrome c and cooling after electroporation may augment the release.

Various cellular stress responses and cell death modalities are triggered in response to anti-cancer therapy. Among these, apoptosis has been shown to induce immunogenic cell death (ICD), a death pathway, which stimulates anti-cancer immune response. ICD is characterized by the release of damage-associated molecular proteins, which induce a proinflammatory immune response once exposed on the cell surface or secreted. Among them, calreticulin exposed on the surface of dying cancer cells is essential for the immunogenicity of apoptosis. It has recently been shown that calreculin translocates to the cell surface in response to nsEP. Thus, apoptosis induced by cooling may cause ICD and potentially stimulate an anti-cancer immune response.

The following paragraphs disclose a second study that further confirms the synergistic effects of combined nsEP and cooling on cell death, even when the nsEP or cooling alone are insufficient to cause cell death on their own.

Study 2: Abstract

Plasma membrane permeabilization by nsEP may cause osmotic imbalance, water uptake, cell swelling and eventual membrane rupture. The present study was aimed to increase the cytotoxicity of nsEP by fostering water uptake and cell swelling. This aim was accomplished by lowering temperature after nsEP application, which delayed membrane resealing and/or suppressed the cell volume mechanisms. Cell diameter in U-937 monocytes exposed to a train of 50, 300-ns pulses (100 Hz, 7 kV/cm) at room temperature and then incubated on ice for 30 min increased by 5.6+/−0.7 µm (40-50%), which contrasted little or no changes (1+/−0.3 µm, <10%) if the incubation was at 37° C. Neither this nsEP dose nor the 30-min cooling caused cell death when applied separately; however, their combination reduced cell survival to about 60% in 1.5-3 hr. Isosmotic addition of a pore-impermeable solute (sucrose) to the extracellular medium blocked cell swelling and rescued the cells, thereby pointing to swelling as a primary cause of membrane rupture and cell death.

Study 2: Introduction

Recent studies have focused on the use of electric pulses of nanosecond duration (nsEP) for tumor ablation by irreversible electroporation (IRE). Mechanisms responsible for nsEP cytotoxicity have been a subject of numerous studies but nonetheless remain just partially understood. Nanosecond EP have been shown to induce both apoptosis and necrosis. In early studies, apoptosis was claimed to be the prevailing mode of cell death. Indeed, various cell types exposed to lethal doses of nsEP showed apoptotic hallmarks such as caspase activation, cytochrome C release in the cytoplasm, poly-ADP ribose polymerase (PARP) cleavage, and DNA fragmentation. Recently a role for cell swelling has become apparent as a critical component of the cell death caused by nsEP. The increase in cell volume or cell swelling is a morphological feature that characterizes the necrotic cell death. Necrosis is a separate or even a predominant mode of nsEP-induced cell death. The primary cause of necrosis was the persistent plasma membrane permeabilization (nanoelectroporation) which resulted in the osmotic imbalance, water uptake, and cell swelling culminating in the membrane rupture.

Study II reveals that cooling blocks repairing mechanisms activated by the cell to survive the nsEP insult. The osmotic swelling of nsEP-treated cells is minimized by warming to the physiological temperature (37° C.) and intensified by a transient cooling. Consequently, cooling after nsEP significantly increased the early necrotic cell death even though neither cooling nor nsEP were effective when applied separately. This cell death was prevented by countering the colloid osmotic imbalance by isosmotic replacement of extracellular $Na^+$ and $Cl^-$ with a larger solute (sucrose), which confirms the pathological role of swelling. This suggests that post-nsEP cooling could assist tumor ablation therapies.

Study 2: Materials and Methods

Cell Line and Media

As in Study I, experiments were performed using the human monocyte lymphoma U-937 cell line (ATCC, Manassas, Va.). Cells were cultured in RPMI-1640 medium with L-glutamine (ATCC), supplemented with 10% (v/v) fetal bovine serum (Atlanta Biologicals, Norcross, Ga.), 100 U/ml penicillin and 0.1 mg/ml streptomycin (Mediatech Cellgro, Herdon, Va.).

nsEP Exposure Method

All nsEP exposures were performed at room temperature. Cells were resuspended at 1.2×106 cell/ml in fresh RPMI medium, and 100 µl samples of this suspension were aliquoted to 1 mm gap electroporation cuvettes (BioSmith, San Diego, Calif.) for nsEP exposures.

Trapezoidal pulses of 300 ns duration and 700 V amplitude from an AVTECH AVOZ-D 2-B-ODA generator (AVTECH Electrosystems, Ottawa, Ontario, Canada) were delivered to electroporation cuvettes via a 50- to 10-Ohm transition module (AVOZ-D2-T, AVTECH Electrosystems) modified into a cuvette holder. Pulse trains of predetermined duration at the selected repetition rate of 100 Hz were triggered externally from a model S8800 stimulator (Grass Instrument Co., Quincy, Mass.).

The pulse amplitude and shape were monitored using a 500 MHz, 5 GS/s TDS 3052B oscilloscope (Tektronix, Wilsonville, Oreg., USA).

Post-nsEP Exposure Protocols

Figure 12B:
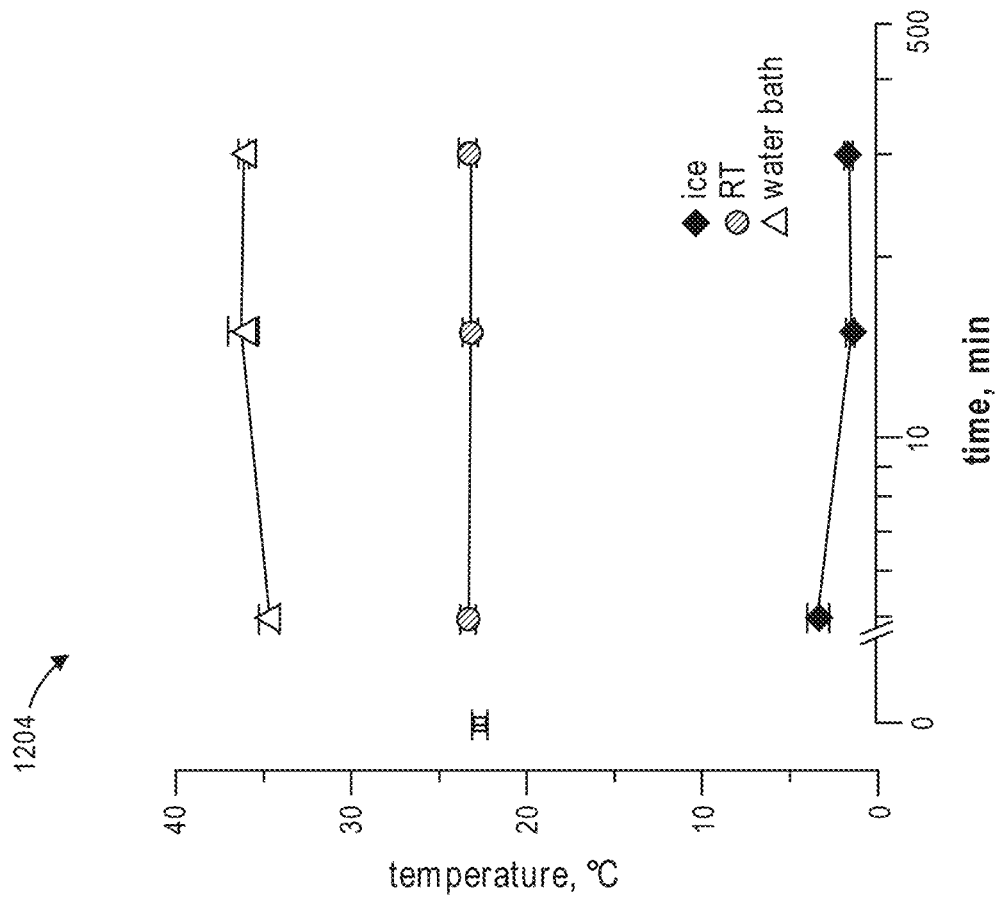
FIG. 12B illustrates a graph of temperature measurements, associated with the effects of temperature on nsEP-exposed cells, in accordance with embodiments of the present disclosure.
Figure 12A:
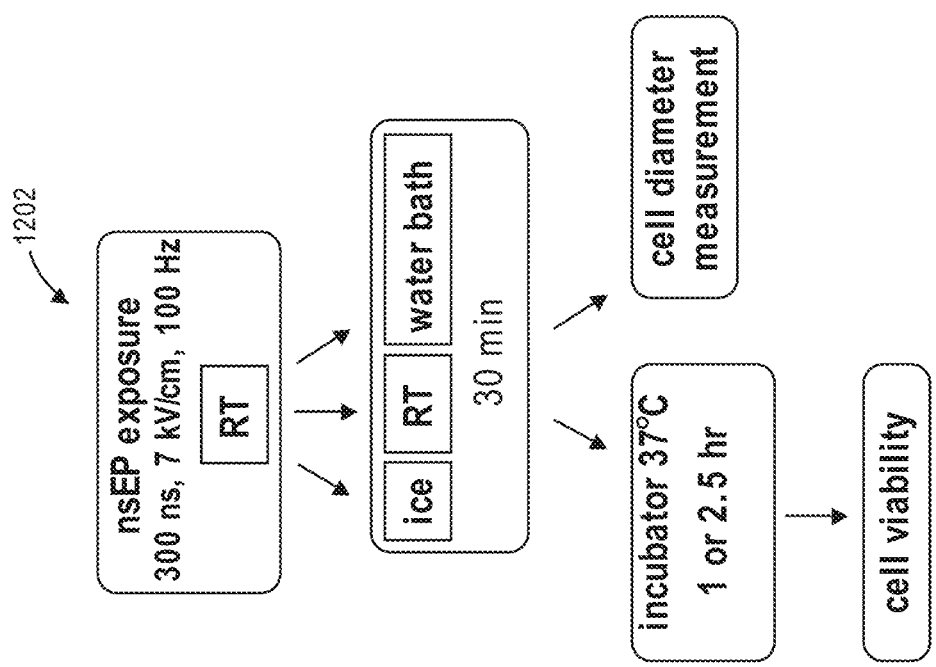
FIG. 12A illustrates an experimental flow chart associated with the effects of temperature on nsEP-exposed cells, in accordance with embodiments of the present disclosure.

FIG. 12A illustrates an experimental flow chart 1202 associated with measuring the effects of temperature on nsEP-exposed cells. Cell samples were exposed at room temperature (RT) to nsEP, with the pulses having 300 ns duration, 100 Hz at 7 kV/cm. Immediately following nsEP exposure, samples were diluted 1:1 with either ice cold, or room temperature, or 37° C. RPMI medium. Cuvettes were then placed on ice, or in a water bath at 37° C., or left at room temperature (RT) for 30 min. After 30 min, cell diameters are measured and samples are moved to standard cell culture condition. Cell survival was assessed at either 1.5 or 3 hr post-nsEP exposure.

The temperature of the samples in the different settings was measured using a thermocouple thermometer (Pysitemp, Clifton, N.J.). Sample temperature by the end of 30-min incubation on ice, at RT, and in the waterbath averaged, respectively, 1.6, 23.3, and 36.1° C. (FIG. 12). These measured temperatures are shown in graph 1204 of FIG. 12B, which shows for the different incubation conditions (ice, RT and water bath) the temperatures measured at 5, 15 and 30 min in accordance with the experimental flowchart 1202 shown in FIG. 12A. Mean+/-s.e. for 3 independent measurements.

To block cell swelling, sucrose was administered to the cells. Sucrose, a nanopore-impermeable sugar, was shown to prevent the osmotic water uptake caused by nsEP.

Immediately following nsEP or sham treatment, samples were mixed 7:3 with an isosmotic (290 mOsm/kg) sucrose solution in water to yield the fractional osmolality due to sucrose of 87 mOsm/kg. Such a fraction of sucrose was found to provide colloid-osmotic balance to the cytosol thus preventing swelling of permeabilized cells. Parallel controls were diluted with either RPMI or NaCl at the same proportion. NaCl does not prevent water uptake and therefore served as a control for the equivalent dilution of the medium.

Cell Diameter Measurement

Cell samples were loaded into a counting chamber of Cellometer Vision (Nexcelom Bioscience LLC, Lawrence, Mass.) and imaged by brightfield transillumination. The diameters of 300-500 cells per sample were automatically measured from the image and logged using Cellometer software.

Viability Assays

Cell survival was measured either at 3 hr after nsEP exposure using the resazurin-based metabolic assay Presto Blue (Life Technologies, Grand Island, N.Y.) or at 1.5 hr using the fluorescent dye exclusion/quenching assay with acridine orange and propidium iodide (AO/PI assay). Both assays were described in details previously (Pakhomova et al. 2014; Pakhomova et al. 2013).

For the Presto blue assay, immediately following the incubation at different temperatures, the samples were diluted with fresh medium to $3\times10^5$ cells/ml and aliquoted into a 96-well plate, in triplicates at $30\times10^3$ cell/well. The plates were kept in the incubator for 30 min before the addition of 10 µl of Presto Blue reagent for 2 hr. The plate was read with a Synergy 2 microplate reader (BioTek, Winooski, Vt.), with excitation/emission settings at 530/590 nm. The triplicate data were averaged, corrected for the background, and considered as a single experiment.

In the AO/PI assay, acridine orange (Sigma-Aldrich, St. Louis, Mo.) is permeable to both live and dead cells and fluoresces green (exc./em. 475/535 nm). Propidium iodide (Sigma-Aldrich) enters dead cells with compromised membranes and fluoresces red (exc./em. 525/595 nm). Immediately before measurements, 20 µl of the cell samples were mixed with equal volume of staining solution (0.5 µg/ml AO and 100 µg/ml PI in PBS). Samples were loaded into a counting chamber and analyzed using Cellometer Vision with two-channel cell fluorescence detection. Live cells fluoresced bright green while in dead cells the AO emission was quenched by the PI uptake.

Depending on the experiment, data were normalized to parallel sham controls, or to the value of a control sample neither exposed to pulses nor to changes in temperature, or presented as live cell fraction.

Statistical Analysis

Data are presented as mean+/-SE for n independent experiments. Statistical analyses were performed using a two-tailed t-test where $p<0.05$ was considered statistically significant. Statistical calculations, including data fits, and data plotting were accomplished using Grapher 11 (Golden Software).

Study 2: Results

Post-nsEP Cooling Increases Cell Swelling

Figure 13:
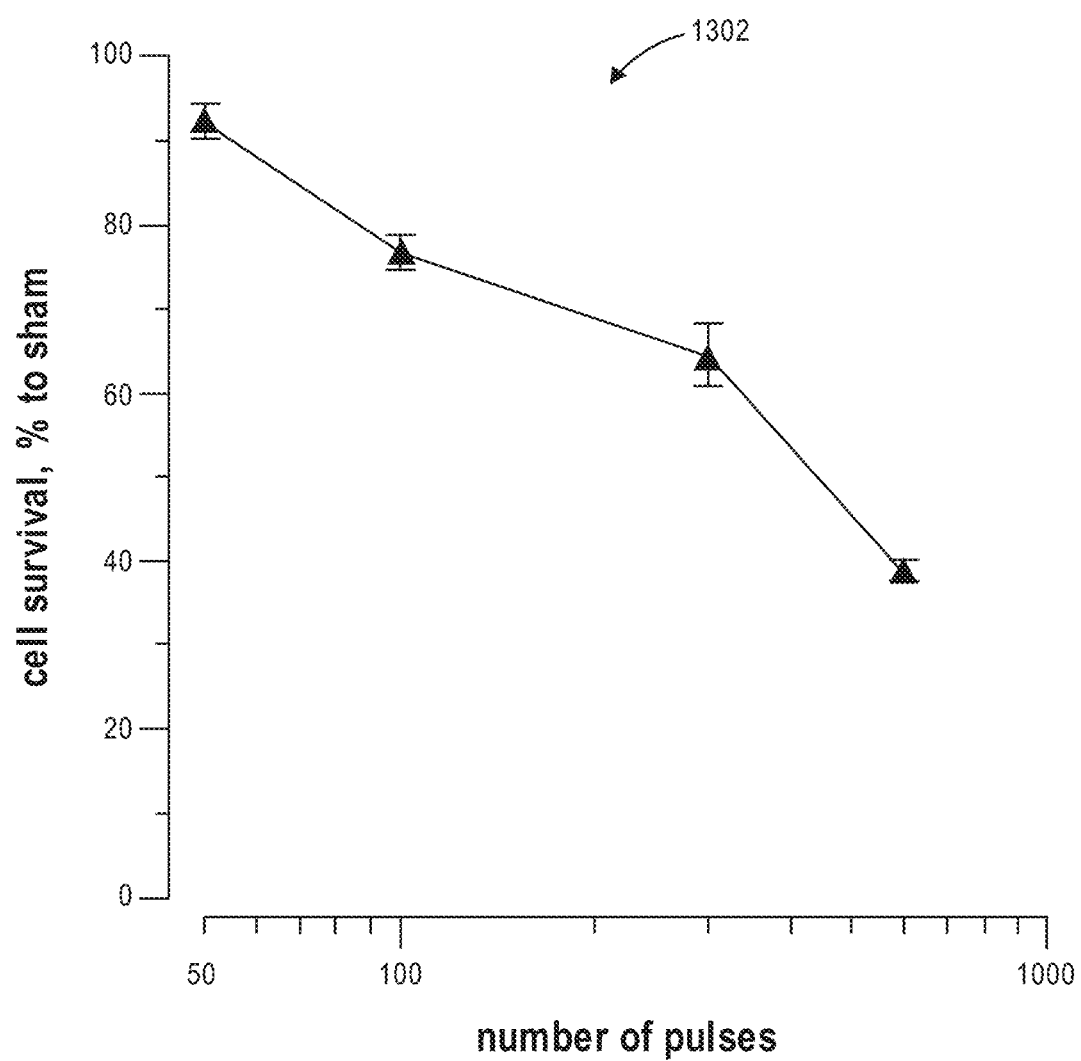
FIG. 13 illustrates graphs depicting the effect of pulse number on early U-937 cell death, in accordance with embodiments of the present disclosure.
Figure 14A:
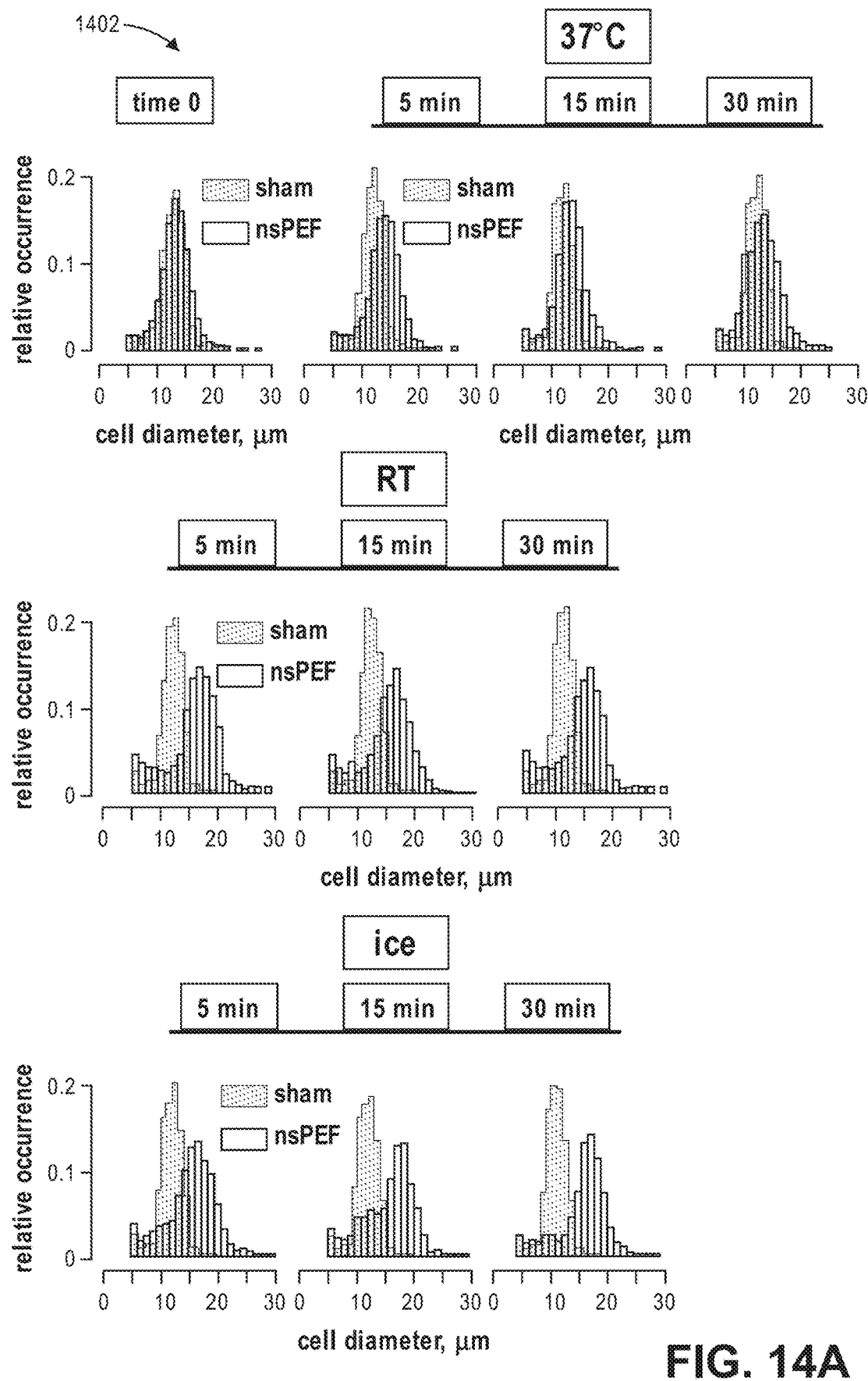
FIGS. 14A-14C illustrate graphs depicting how temperature affects nsEP-induced cell swelling, in accordance with embodiments of the present disclosure.
Figure 14B:
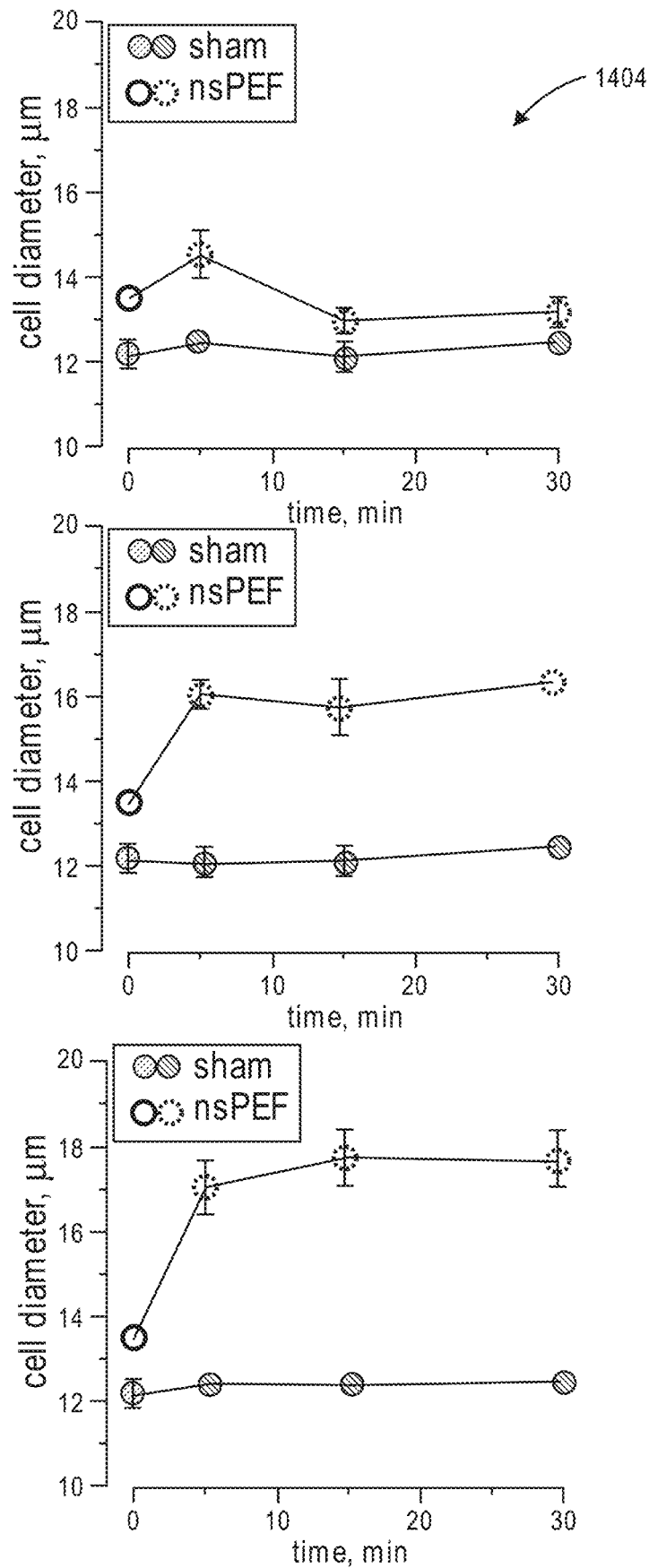
Figure 14C:
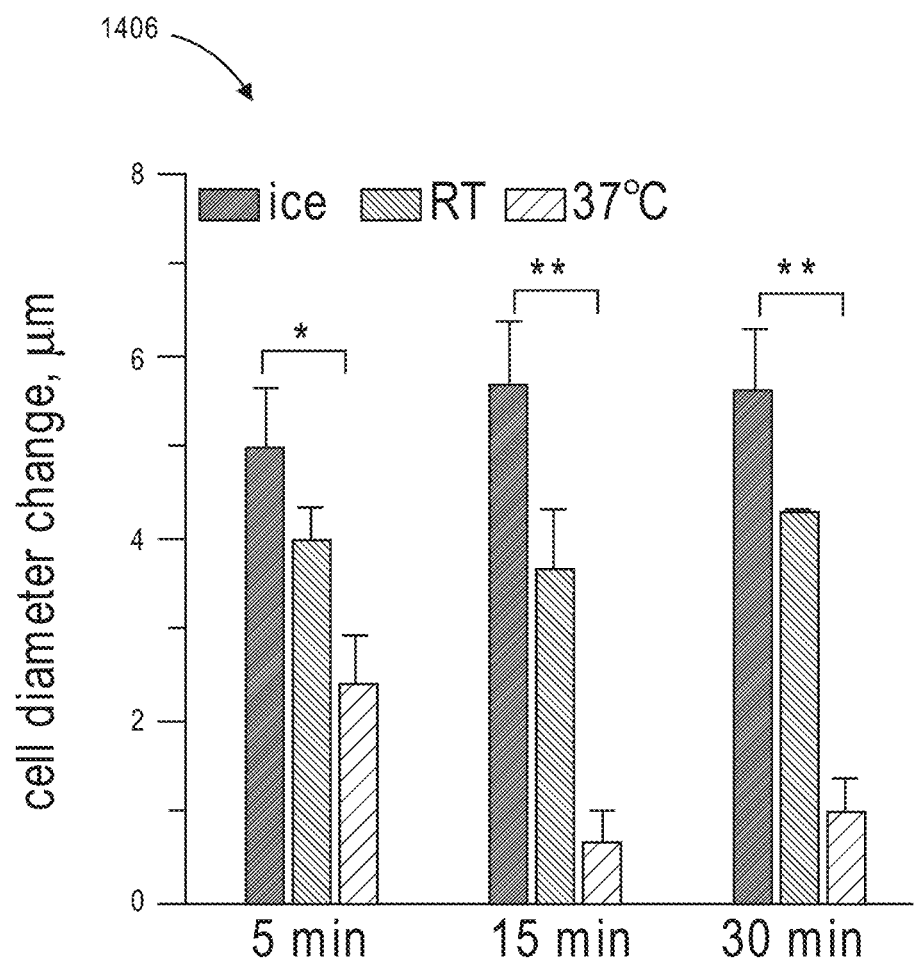

Before investigating whether temperature affects EP-induced cell swelling and resulting necrosis, cell survival was measured at 3 hr after exposure to different numbers of 300-ns, 7 kV/cm pulses delivered at 100 Hz. Cells were exposed to increasing numbers of 300 ns pulses (100 Hz at 7 kV/cm). Immediately after exposure, all samples were moved to the 37° C. incubator and cell survival was assessed in 3 hr using the metabolic activity assay Presto blue. Mean+/-s.e. for 3 independent experiments. FIG. 13 illustrates the effect of pulse number on cell survival early U-937 cell death. Graph 1302 of FIG. 13 plots the cell survival rate against the number of pulses the cells were exposed to. As can be seen, there is a relationship between an increase in the number of pulses and the decrease in survival rate of the cell. A dose of 50 pulses, which caused no significant decrease of viability, was chosen to study the effect on cell size of different post-nsEP temperature incubations. All cell samples were exposed to nsEP at room temperature (RT). Immediately after the exposure, samples were either placed on ice, or moved into a 37° C. water bath, or left at RT, and cell diameters were measured at 5, 15 and 30 min post nsEP treatment. Parallel sham-exposed samples were incubated at the different temperatures the same way. FIGS. 14A-14C show, for the different temperature incubations, the time dynamics of cell volume change following nsEP treatment and how temperature affects nsEP-induced cell swelling. In graphs 1402 of FIG. 14A, the bar charts show, for the different temperatures, the frequency distribution of cell diameter values at the indicated time intervals after nsPEF exposure. Graphs 1404 of FIG. 14B show, for each temperature, the cell diameter mode value as a function of time after treatment. Sham values are shown as filled symbols. Graph 1406 of FIG. 14C shows, for each temperature, the cell diameter change over sham. Mean+/-s.e. for 3 independent experiments. *p<0.05, ** p<0.01 for the difference between nsEP+cooling and nsEP+37° C. Note the increase and persistent cell swelling in samples kept at RT and on ice. Between these figures, it can be seen that the diameter of the sham-exposed samples did not depend on the different temperature conditions; the distribution of cell diameters was bell-shaped with mode at 12.4 µm.

The post exposure incubation temperature had major impact on nsEP-induced swelling. At 5 min post nsEP treatment, the modal diameter of cells incubated on ice increased to 17.2+/−0.6 µm (n=3) but only to 14.5+/−0.5 µm (n=3) in cells incubated at 37° C. (p<0.05, FIGS. 14B and 14C). Cells incubated at RT showed an intermediate volume increase, to 16.0+/−0.3 µm (n=3) This impact of temperature became even more prominent at 15 and 30 min after nsEP, when the cells on ice remained swollen but those kept at 37° C. restored the initial volume.

Such effects of temperature on swelling of electroporated cells indicate faster membrane resealing and/or engaging of the active volume control at 37° C., whereas lowering the temperature inhibits these rescue mechanisms.

Cooling Increases Early Cell Death in U-937 Cells Subjected to nsEP Exposure

Figures 15A, 15B:
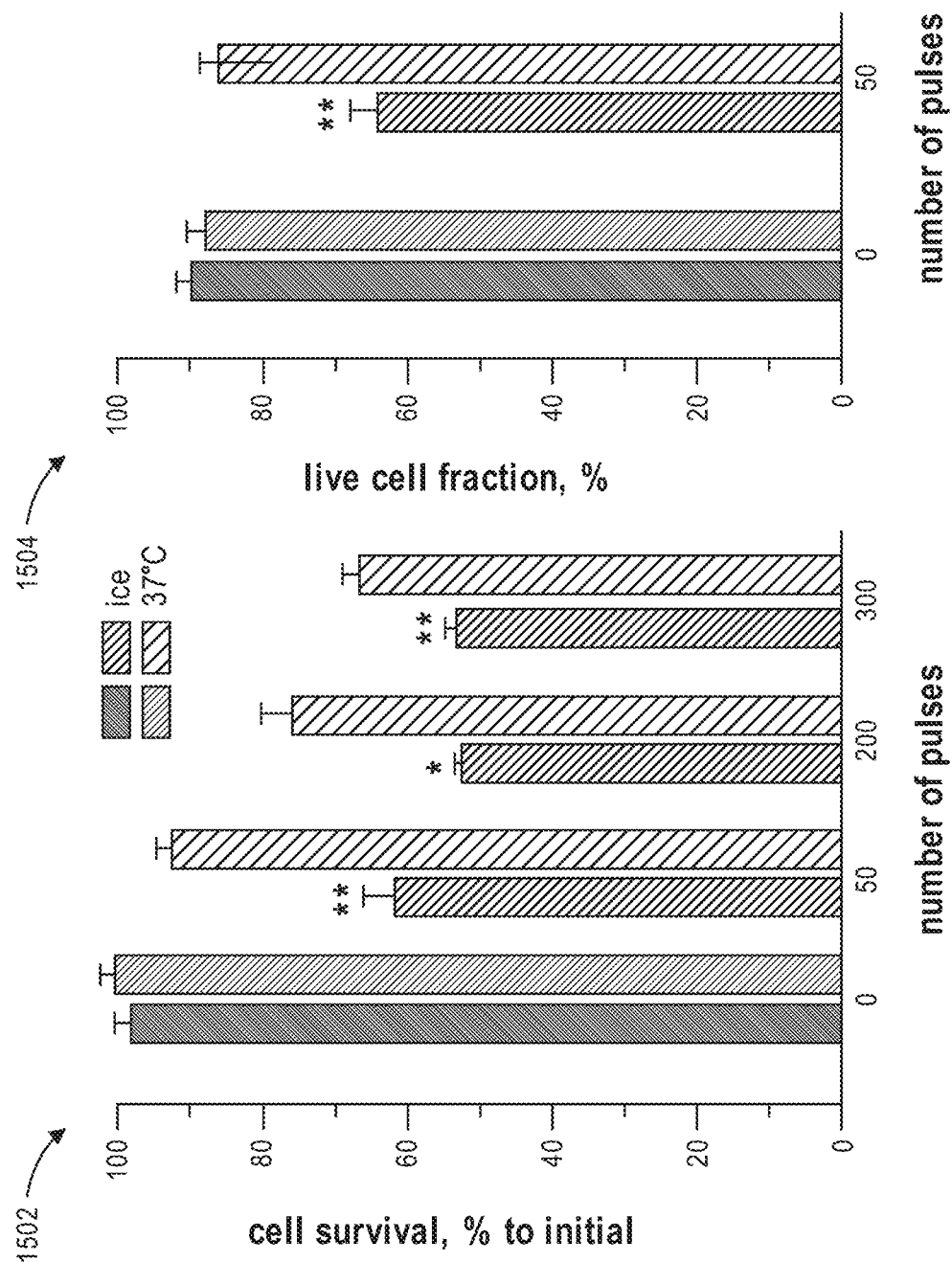
FIGS. 15A-15B illustrate graphs depicting how post-nsEP cooling increases early cell death, in accordance with embodiments of the present disclosure.

The impact of cooling on nsEP-induced cell swelling prompted investigation of whether there was also an effect on the early cell survival. Graph 1502 of FIG. 15A and graph 1504 of FIG. 15B represent the data from two independent sets of experiments in which cell survival was measured at different times after nsEP exposure and with different detection assays. Cell samples were treated with 50, 200 or 300 pulses (300 ns, 7 kV/cm, 100 Hz) and immediately placed at 37° C. or on ice for 30 min before their transfer to the incubator. At 3 hr after nsEP treatment, cell survival was measured by a resazurin-based cell metabolic activity assay. As shown in FIG. 15A, cell viability was measured at 3 hr after nsEP exposure by the Presto blue assay and normalized to the value of a control sample neither exposed to pulses nor to changes in temperature. In graph 1504 of FIG. 15B, cell survival was measured by the AO/PI assay at 1.5 hr post exposure. Data are presented as live cell fraction. Parallel sham-exposed controls were treated the same way and are shown by filled columns. Mean+/−s.e. n=8, (A) or n=6 (B). *p<0.01, **p<0.001 for the difference of nsEP+cooling from nsEP+37° C. From the two figures, it can be seen that the 30-min incubation on ice was not harmful by itself and did not affect the survival of sham-exposed cells. Conversely, the same incubation of nsEP-treated cells clearly augmented the cell killing, especially at the lowest dose of 50 pulses which was not cytotoxic without cooling. With 200 and 300 pulses, the nsEP+cooling condition was still more efficient, however cell death started to increase also in nsEP-treated samples which underwent the 37° C. incubation.

The strong synergistic effect of nsEP (50 pulses) and cooling was confirmed using the AO/PI membrane integrity assay to assess cell death. Compared to the resazurin reduction based assay, the protocol for the AO/PI assay is much faster allowing to measure cell survival at earlier time points. Already at 1.5 hr after treatment, nsEP+cooling caused 38% cell death. Such rapid disruption of the cell membrane preceded by cell swelling point to the necrotic mechanism of cell death.

Sucrose Blocks Cell Swelling and Eliminates the Effect of Cooling on Post-nsEP Cell Survival Electroporated cells take up water and swell because of the colloid osmotic pressure generated by the large intracellular solutes which remain membrane impermeable. This pressure can be counterbalanced by the presence in the extracellular milieu of pore-impermeable solutes such as sucrose.

Figure 16A:
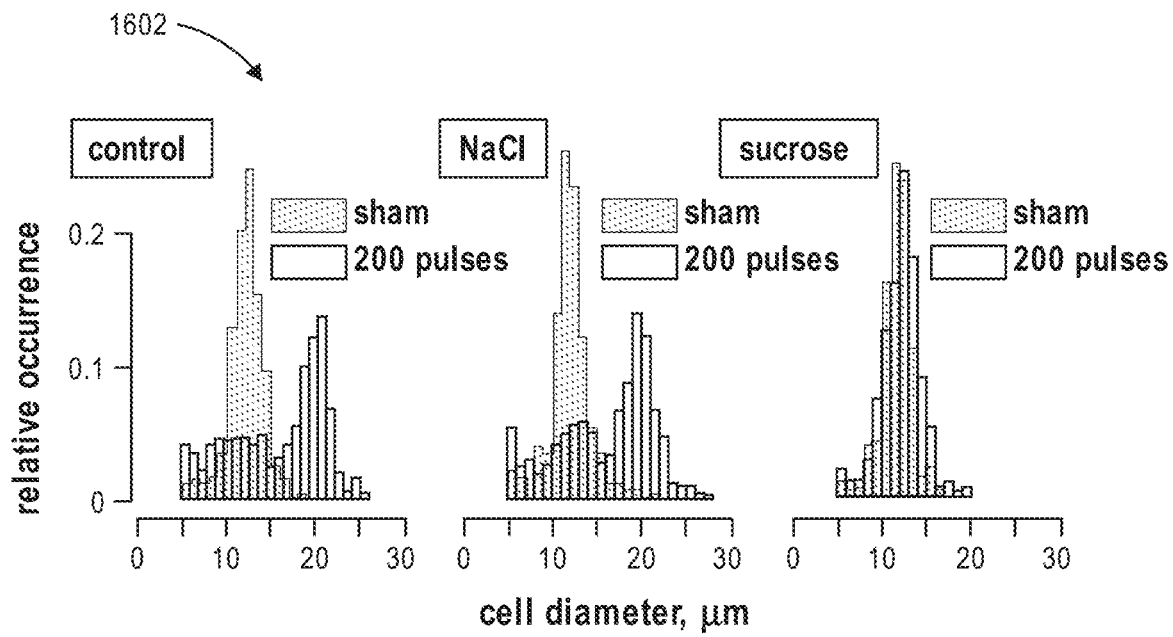
FIGS. 16A-16B illustrate graphs depicting how sucrose inhibits cell swelling and early cell death caused by combining nsEP with cooling, in accordance with embodiments of the present disclosure.
Figure 16B:
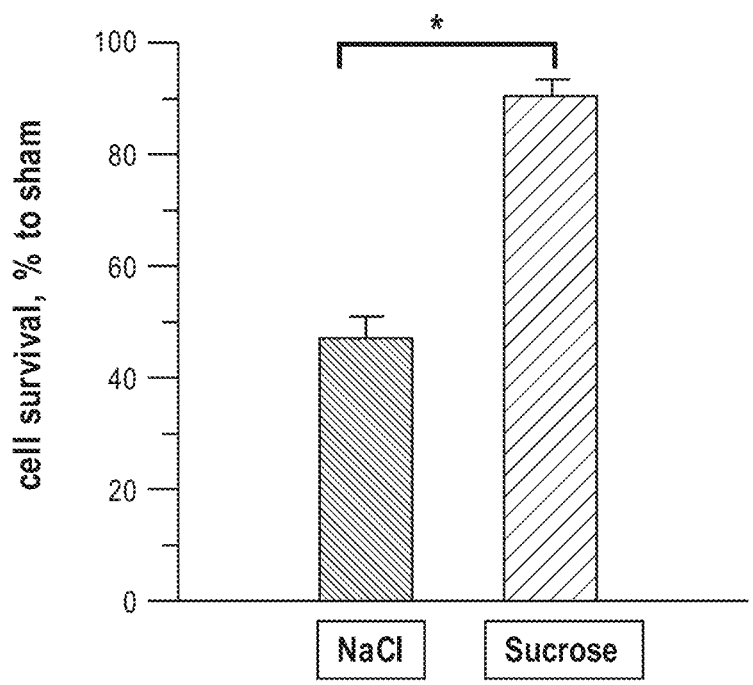

FIGS. 16A-16B show how sucrose affects cell swelling and cell death induced by combining nsEP with cooling. In these set of experiments, a higher number of pulses is used to induce even more cell swelling. All cell samples were exposed to 200 pulses (300 ns, 7 kV/cm, 100 Hz) in RPMI medium. Immediately after exposure, the samples were mixed with either sucrose or NaCl solution (control) to yield an 87 mOsm/kg final osmolarity due to sucrose or NaCl. All samples were then placed on ice. Sham-exposed cell samples that served as controls were treated the same way. After 30 min incubation, aliquots were collected to measure cell diameters. The remaining samples were diluted with 400 µl of RPMI medium and moved into the incubator (37° C.) for 2.5 hr before assessing cell survival.

Graph 1602 of FIG. 16A shows the effect of sucrose on the cell diameters, whereas the graph 1604 of FIG. 16B shows its effect on cell survival at 3 hr post nsEP exposure. The survival is in % to sham-exposed parallel control. Mean+/−s.e. n=4, *p<0.001. Note fast cell swelling in RPMI+NaCl which correlates with decreased survival, whereas in the RPMI+sucrose there is no swelling and complete protection from cell death.

The dilution of RPMI with sucrose completely prevented cell swelling whereas a similar dilution with NaCl had no effect. The fact that sucrose also inhibited the reduction of cell survival suggests that the colloid osmotic swelling was indeed the primary cause of membrane rupture and early cell death.

Study 2: Discussion

To date the effect of temperature after EP exposure has been investigated only in context of electrotransfection protocol optimization. In the past the most commonly used electrotransfer conditions called for pre-incubation, pulsation and post-pulsation incubation at 4° C. (Potter 1993). However, the literature was contradictory especially about the postpulsation step with several groups reporting that the post-pulse incubation at low temperature was detrimental (Andreason and Evans 1989; Chu et al. 1987; Rols et al. 1994). Later studies revealed that DNA is electrophoretically transferred across the electropore during pulsing. This finding suggests that prolonging the permeabilized state of the plasma membrane at low temperature is not required to increase the transfection efficiency but rather damages the cell.

The data of the present disclosure shows that combining cooling with nsEP augments osmotic swelling mediated necrosis. It appears that cooling blocks rescue mechanisms such as membrane resealing and active volume control; thereby it aggravates the loss of essential cell metabolites like ATP and augments damage from the entry of potentially toxic ions, e.g., $Ca^{2+}$.

In addition to the effect on membrane resealing, low temperature may block active volume control mechanisms. In response to osmotic swelling cells activate regulatory volume decrease mechanisms (RVD). As discussed elsewhere (Okada et al. 2001), RVD occurs by loss of $K^+$, $Cl^-$ and organic solutes leading to the efflux of water. In the face of a swelling emergency, cells activate the available $K^+$ channels and a variety of anion channels (Hoffmann and Pedersen 1998). In human lymphocytes RVD has been shown to be faster and more complete at 37° C. compared to 25° C. (Lee et al. 1988). Interestingly, the behavior of $K^+$ channels in human T lymphocytes has also been shown to be temperature dependent suggesting that the slower RVD at 25° C. may be explained by the effect of temperature on K$^+$ channels (Pahapill and Schlichter 1990).

In medical applications, cooling has been used only to improve thermal dissipation. The only surgical technique exploiting low temperature is cryosurgery which, however, uses high subzero freezing conditions to ablate tissue. Tumor treatment with nsEP is a promising approach for cancer ablation and cooling can be easily applied post exposure to surface lesions and could be an efficient approach to increase the ablation zone without extra pain or damage.

It is to be understood that other embodiments than those described above may be utilized and structural or logical changes may be made without departing from the scope of the present disclosure. The Detailed Description, therefore, is not to be taken in a limiting sense, and the scope of the present disclosure is defined by the appended claims. It will also be apparent that although the methodology described above as discrete steps, one or more steps may be combined or even deleted, without departing from the intended functionality of the embodiments of the disclosure. Moreover, although individual features of one embodiment may be discussed or shown in the drawings of the one embodiment and not in other embodiments, it should be apparent that individual features of one embodiment or figure may be combined with one or more features of another embodiment or figures, or features from a plurality of embodiments. It will be apparent that the number of steps that are utilized for such methods are not limited to those described above. Also, the methods do not require that all the described steps are present. Although the methodology described above as discrete steps, one or more steps may be added, combined or even deleted, without departing from the intended functionality of the embodiments.

What is claimed is:

1. A method of tissue ablation comprising:
    applying an electrode to an abnormal growth of a subject, wherein the electrode is electrically coupled to a generator, and wherein the electrode is configured to conduct sub-microsecond electric pulses produced by the generator;
    pulsing an electric field through the abnormal growth for a first duration using the sub-microsecond electric pulses conducted by the electrode, wherein the electric field has an intensity of more than 1 kV/cm, and wherein a width of each of the sub-microsecond electric pulses is between 1 ns and 1000 ns; and
    after initiating the pulsing, begin cooling the abnormal growth for a second duration such that pores opened by the electric field pulses seal up slower than if no cooling had occurred,
    wherein the steps of pulsing and cooling synergistically stimulate apoptosis of cells in the abnormal growth.

2. The method of claim 1, wherein the cooling step prolongs a permeabilized state of cellular membranes, such that the intensity of the electric field is sufficient to trigger apoptosis of cells in the abnormal growth, and wherein the intensity of the electric field is reduced compared to a level of intensity of the electric field otherwise required to trigger the apoptosis without the cooling step.

3. The method of claim 1, wherein the cooling step further comprises lowering a temperature of the abnormal growth to be between zero degrees Celsius and twenty degrees Celsius, thereby inhibiting resealing of pores opened by the electric pulses.

4. The method of claim 3, wherein the cooling step further comprises lowering the temperature of the abnormal growth to approximately two degrees Celsius.

5. The method of claim 1, wherein the second duration is at least five minutes.

6. The method of claim 1, wherein the second duration is under one hour.

7. The method of claim 1, wherein the second duration is approximately between fifteen and thirty minutes.

8. The method of claim 1, wherein cooling the abnormal growth for the second duration occurs immediately following the first duration.

9. The method of claim 1, wherein cooling the abnormal growth for the second duration occurs at least in part during the first duration.

10. The method of claim 1, wherein the synergistic stimulation caused by the pulsing and cooling steps results in at least a 25% reduction in treated tissue cells survival compared to pulsing alone without cooling.

11. The method of claim 1, wherein the intensity of the electric field is between 5 to 7 kV/cm.

12. The method of claim 1, wherein the sub-microsecond electric pulses are pulsed at a frequency of about 0.1 to 500 Hz.

13. The method of claim 1, wherein the synergy of the pulsing and cooling steps provides substantially the same ablation efficiency while allowing one or more of the following: 1) lowering pulse voltage, 2) lowering pulse numbers, or 3) increasing a distance between the electrodes.

14. The method of claim 1, wherein the synergistic stimulation caused by the pulsing and cooling steps minimizes side effects of ablation.

15. The method of claim 1, wherein the cooling step is performed using an ice-pack.

16. The method of claim 1, wherein the abnormal growth comprises one of: a malignant tumor, a pre-malignant tumor, or a benign tumor.

17. The method of claim 1, wherein cooling the abnormal growth is achieved through perfusion by injecting saline into the subject.

18. A method of tissue ablation, comprising:
    applying a plurality of nanosecond electric field pulses greater than 1,000 V/cm to a tissue on or in a subject, the plurality of nanosecond electric field pulses having intensity sufficient to open pores in cell membranes of the tissue; and
    after initiating applying the plurality of nanosecond electric field pulses, beginning cooling the tissue such that the pores opened by the electric field pulses seal up slower than if no cooling had occurred,
    wherein the steps of applying the plurality of pulses and cooling synergistically stimulate apoptosis of cells in the tissue resulting in at least a 25% reduction in survival of the cells in the tissue, as compared to survival of the cells in the tissue in a comparable application of the plurality of nanosecond electric field pulses performed without cooling the tissue.

19. The method of claim 18, wherein applying the plurality of pulses and cooling synergistically stimulate apoptosis of cells in the tissue resulting in between a 25% to 80% reduction in survival of the cells in the tissue, as compared to survival of the cells in the tissue in the comparable application of the plurality of nanosecond electric field pulses performed without cooling the tissue.

20. The method of claim 18, wherein the intensity of the plurality of electric field pulses does not cause necrosis.

21. The method of claim 18, wherein cooling the tissue prolongs a permeabilized state of the cell membranes, such that the intensity of the plurality of electric field pulses is sufficient to trigger apoptosis of the cells in the tissue, and wherein the intensity of the plurality of electric field pulses is reduced compared to a level of intensity of the electric field pulses otherwise required to trigger the apoptosis without the cooling.

22. The method of claim 18, wherein cooling the tissue further comprises lowering a temperature of the tissue to be between zero degrees Celsius and twenty degrees Celsius, thereby inhibiting resealing of the pores opened by the plurality of electric field pulses.

23. The method of claim 22, wherein cooling the tissue further comprises lowering the temperature of the tissue to approximately two degrees Celsius.

24. The method of claim 18, wherein applying the plurality of nanosecond electric field pulses is performed for a first duration, wherein cooling the tissue is performed for a second duration, and wherein the second duration occurs at least in part during the first duration.

25. The method of claim 18, wherein cooling the tissue is achieved through perfusion by injecting saline into the subject.

* * * * *